United States Patent
Kühnert et al.

(10) Patent No.: US 8,367,700 B2
(45) Date of Patent: Feb. 5, 2013

(54) SUBSTITUTED 4-(1,2,3,4-TETRAHYDROISOQUINOLIN-2-YL)-4-OXOBUTYRIC ACID AMIDE AS KCNQ2/3 MODULATORS

(75) Inventors: Sven Kühnert, Düren (DE); Gregor Bahrenberg, Monschau-Konzen (DE); Beatrix Merla, Aachen (DE); Klaus Schiene, Jüchen (DE); Wolfgang Schröder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 429 days.

(21) Appl. No.: 12/635,800

(22) Filed: Dec. 11, 2009

(65) Prior Publication Data
US 2010/0152234 A1 Jun. 17, 2010

Related U.S. Application Data

(60) Provisional application No. 61/138,269, filed on Dec. 17, 2008.

(30) Foreign Application Priority Data

Dec. 17, 2008 (EP) .................................... 08021880

(51) Int. Cl.
*A61K 31/4709* (2006.01)
*A61P 25/00* (2006.01)
*C07D 217/12* (2006.01)
(52) U.S. Cl. ....................................... 514/307; 546/144
(58) Field of Classification Search .................. 514/307; 546/144
See application file for complete search history.

(56) References Cited

U.S. PATENT DOCUMENTS

2002/0128277 A1 9/2002 Dworetzky et al.

FOREIGN PATENT DOCUMENTS

| AU | 2009335340 | 8/2011 |
|---|---|---|
| CA | 2747094 | 7/2010 |
| CN | 102256947 | 11/2011 |
| EP | 2358681 | 8/2011 |
| KR | 20110100651 | 9/2011 |
| MX | 2011006384 | 7/2011 |
| WO | 2008/046582 A1 | 4/2008 |
| WO | 2010075973 | 7/2010 |

OTHER PUBLICATIONS

Bennett et al; "A peripheral mononeuropathy in rat that produces disorders of pain sensation like those seen in man"; Pain, 33 (1988) pp. 87-107.
Blackburn-Munro et al; "The anticonvulsant retigabine attenuates nociceptive behaviours in rat models of persistent and neuropathic pain": European Journal of Pharmacology 460 (2003) pp. 109-116.
Dencker et al; "Effect of the new antiepileptic drug retigabine in a rodent model of mania": Epilepsy & Behavior 12 (2008) pp. 49-53.
Dost et al; "The anti-hyperalgesic activity of retigabine is mediated by KCNQ potassium channel activation" ; Naunyn-Schmiedeberg's Arch Pharmacol (2004) 369; pp. 382-390.
Dubuisson et al; "The formalin test: a quantitative study of the analgesic effects of morphine, meperidine, and brain stem stimulation in rats and cats": Pain, 4 (1977) pp. 161-174.
Gribkoff; "The therapeutic potential of neuronal KCNQ channel modulators"; Expert Opinion, Central & Peripheral Nervous Systems; Ashley Publications Ltd. 2003; pp. 737-748.
Hansen et al; "The neuronal KCNQ channel opener retigabine inhibits locomotor activity and reduces forebrain excitatory responses to the psychostimulants cocaine, methylphenidate and phecyclidine"; European Journal of Pharmacology 570 (2007); pp. 77-88.
Kim et al; "An experimental model for peripheral neuropathy produced by segmental spinal nerve ligation in the rat" Pain, 50 (1992) pp. 355-363.
Korsgaard et al; "Anxiolytic effects of maxipost (BMS-204352) and retigabine via activation of neuronal Kv7 channels"; The Journal of Pharmacology and Experimental Therapeutics; Vo. 314, No. 1, pp. 282-292, (2005).
Miceli et al; "Molecular pharmacology and therapeutic potential of neuronal Kv7-modulating drugs"; Current Opinion in Pharmacology 2008, 8, pp. 65-74.
Nielsen et al; "Pharmacological characterisation of acid-induced muscle allodynia in rats"; European Journal of Pharmacology 487 (2004) pp. 93-103.
Passmore et al; "KCNQ/M currents in sensory neurons: significance for pain therapy"; The Journal of Neuroscience, Aug. 6, 2003, 23(18), pp. 7227-7236.
Richter et al; "Antidystonic effects of Kv& (KCNQ) channel openers in the dt sz mutant, an animal model of primary paroxysmal dystonia": British Journal of Pharmacology (2006) 149, pp. 747-753.
Streng et al; "Urodynamic effects of K+ channel (KCNQ) opener retigabine in freely moving, conscious rats": The Journal of Urology, vol. 172, Nov. 2004, pp. 2054-2058.
Wickenden et al; "KCNQ potassium channels: drug targets for the treatment of epilepsy and pain"; Expret Opinion, Monthly focus: Central & Peripheral Nervous Systems; Ashley Publications Ltd. 2004; pp. 457-.
Stafstrom et al., Nature Reviews, 10: 729-730 (2011).

*Primary Examiner* — Yong Chu
(74) *Attorney, Agent, or Firm* — Norris McLaughlin & Marcus, P.A.

(57) ABSTRACT

The invention relates to substituted tetrahydroisoquinolinyl-4-oxobutyric acid amides, methods for the preparation thereof, medicinal products containing these compounds and the use of these compounds for the preparation of medicinal products.

13 Claims, No Drawings

SUBSTITUTED 4-(1,2,3,4-TETRAHYDROISOQUINOLIN-2-YL)-4-OXOBUTYRIC ACID AMIDE AS KCNQ2/3 MODULATORS

This application claims priority under 35 U.S.C. §119 of EP Application No. 08021880.3, filed Dec. 17, 2008, and under 35 U.S.C. §119(e) of U.S. Provisional Application No. 61/138,269, filed Dec. 17, 2008.

The invention relates to substituted tetrahydroisoquinolinyl-4-oxobutyric acid amides, methods for the preparation thereof, medicinal products containing these compounds and the use of these compounds for the preparation of medicinal products.

The treatment of pain, in particular neuropathic pain, is of great importance in medicine. There is a worldwide need for effective pain therapies. The urgent need for action to find targeted, patient-appropriate treatment for chronic and non-chronic pain conditions, this being understood as the successful and satisfactory treatment of pain for the patient, is also documented in the large number of scientific works that have been published in recent times in the field of applied analgesics and basic research into nociception.

A pathophysiological feature of chronic pain is the over-excitability of neurons. Neuronal excitability is decisively influenced by the activity of $K^+$ channels, since these significantly determine the resting potential of the cell and hence the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarisation of the cell membrane and, accompanying this, to a decrease in the electrical excitability of these neurons. KCNQ2/3-expressing neurons of the dorsal root ganglia are involved in the transmission of nociceptive stimuli from the periphery into the spinal cord (Passmore et al., J Neurosci. 2003; 23(18):7227-36).

It has accordingly been possible to detect an analgesic activity in preclinical neuropathic and inflammatory pain models for the KCNQ2/3 agonist retigabine (Blackburn-Munro and Jensen, Eur J Pharmacol. 2003; 460(2-3):109-16; post et al., Naunyn Schmiedeberg's Arch Pharmacol 2004; 369(4): 382-390).

The KCNQ2/3 $K^+$ channel thus represents a suitable starting point for the treatment of pain; in particular pain chosen from the group consisting of chronic pain, neuropathic pain, inflammatory pain and muscular pain (Nielsen et al., Eur J Pharmacol. 2004; 487(1-3): 93-103), in particular neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety states (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53), dystonia-associated dyskinesias (Richter et al., Br J Pharmacol 2006, 149(6): 747-53).

Substituted tetrahydropyrrolopyrazines having an affinity for the KCNQ2/3 $K^+$ channel are known from the prior art (WO 2008/046582).

There is a need for further compounds having comparable or better properties, not only in regard to affinity for KCNQ2/3 as such (potency, efficacy).

For instance, it can be advantageous to improve the metabolic stability, the solubility in aqueous media or the permeability of the compounds. These factors can have a beneficial effect on oral bioavailability or can alter the PK/PD (pharmacokinetic/pharmacodynamic) profile, which can lead to a more favourable period of action, for example.

A weak or non-existent interaction with transporter molecules, which are involved in the uptake and excretion of medicinal products, can also be taken as an indication of improved bioavailability and at most low medicinal product interaction. Furthermore, interactions with the enzymes involved in the breakdown and excretion of medicinal products should also be as low as possible, since such test results likewise indicate that at most low or even no medicinal product interactions whatsoever are to be anticipated.

It can further be advantageous if the compounds exhibit a high selectivity towards other receptors of the KCNQ family (specificity), for example towards KCNQ1, KCNQ3/5 or KCNQ4. A high selectivity can have a favourable effect on the side-effects profile. It is known, for example, that compounds which (also) bind to KCNQ1 are associated with a high risk of cardiac side effects, for which reason a high selectivity towards KCNQ1 can be desirable. A high selectivity towards other receptors can also be advantageous, however. A low affinity to the hERG ion channel or to the L-type calcium ion channel (phenyl alkylamine, benzothiazepine, dihydropyridine binding sites) can be advantageous, as these receptors are associated with the occurrence of cardiac side effects. Overall an improved selectivity with regard to binding to other endogenous proteins (i.e. receptors or enzymes for example) can lead to an improvement in the side-effects profile and hence to an improved compatibility.

An object of the invention was therefore to provide novel compounds having advantages over the prior art compounds. The compounds should in particular be suitable as pharmacological active ingredients in medicinal products, preferably in medicinal products for the treatment of disorders or diseases which are at least partly mediated by KCNQ2/3 $K^+$ channels.

This object is achieved by the subject matter of the claims.

Surprisingly it has been found that substituted tetrahydroisoquinolinyl-4-oxobutyric acid amides having the general formula (1) given below are suitable for the treatment of pain. It has further surprisingly been found that substituted tetrahydroisoquinolinyl-4-oxobutyric acid amides having the general formula (1) given below also have an excellent affinity for the KCNQ2/3 $K^+$ channel and are therefore suitable for the treatment of disorders or diseases which are at least partly mediated by KCNQ2/3 $K^+$ channels. The substituted tetrahydroisoquinolinyl-4-oxobutyric acid amides act here as modulators, i.e. agonists or antagonists, of the KCNQ2/3 $K^+$ channel.

The invention provides substituted tetrahydroisoquinolinyl-4-oxobutyric acid amides having the general formula (1)

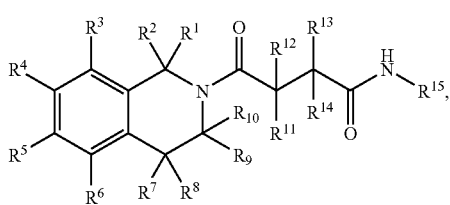

(1)

wherein $R^0$ stands for $C_{1-10}$ alkyl or $C_{2-10}$ heteroalkyl, each saturated or unsaturated, branched or unbranched, unsubstituted or mono- or polysubstituted; $C_{3-7}$ cycloalkyl or heterocyclyl, each saturated or unsaturated, unsubstituted or mono- or polysubstituted; aryl or heteroaryl, each unsubstituted or mono- or polysubstituted; $C_{1-8}$ alkyl-bridged $C_{3-7}$ cycloalkyl or heterocyclyl, each saturated or unsaturated, unsubstituted or mono- or polysubstituted, wherein the alkyl chain can in each case be branched or unbranched, saturated or unsaturated, unsubstituted, mono- or polysubstituted; or $C_{1-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted;

$R^1$ stands for F; Cl; Br; CN; $C_{1-10}$ alkyl, preferably $C_{1-6}$ alkyl, or $C_{2-10}$ heteroalkyl, each saturated or unsaturated, branched or unbranched, unsubstituted or mono- or polysubstituted; $C_{3-7}$ cycloalkyl, preferably $C_{3-6}$ cycloalkyl, or heterocyclyl, each saturated or unsaturated, unsubstituted or mono- or polysubstituted; aryl or heteroaryl, each unsubstituted or mono- or polysubstituted; $C_{1-8}$ alkyl-bridged $C_{3-7}$ cycloalkyl, preferably $C_{3-6}$ cycloalkyl, or heterocyclyl, each saturated or unsaturated, unsubstituted or mono- or polysubstituted, wherein the alkyl chain can in each case be branched or unbranched, saturated or unsaturated, unsubstituted, mono- or polysubstituted; $C_{1-8}$ alkyl-bridged heteroaryl, unsubstituted or mono- or polysubstituted, wherein the alkyl chain can be branched or unbranched, saturated or unsaturated, unsubstituted, mono- or polysubstituted; or $C_{1-8}$ alkyl-bridged aryl, unsubstituted or mono- or polysubstituted, wherein the alkyl chain can be unbranched, saturated or unsaturated, unsubstituted;

$R^2$ stands for H; F; Cl; Br; or $C_{1-10}$ alkyl, saturated or unsaturated, branched or unbranched, unsubstituted or mono- or polysubstituted;

or $R^1$ and $R^2$ together with the carbon atom binding them as ring member form a $C_{3-7}$ cycloalkyl, preferably $C_{3-6}$ cycloalkyl, or heterocyclyl, each saturated or unsaturated, unsubstituted or mono- or polysubstituted, each optionally fused to (hetero)aryl, unsubstituted or mono- or polysubstituted;

$R^3$, $R^4$, $R^5$ and $R^6$ each mutually independently denote H; F; Cl; Br; I; $NO_2$; $CF_3$; CN; $R^0$; C(=O)H; C(=O)$R^0$; $CO_2H$; C(=O)$R^0$; $CONH_2$; C(=O)$NHR^0$; C(=O)N($R^0$)$_2$; OH; $OR^0$; —O—($C_{1-8}$ alkyl)-O—; O—C(=O)—$R^0$; O—C(=O)—O—$R^0$; O—(C=O)—NH—$R^0$; O—C(=O)—N($R^0$)$_2$; O—S(=O)$_2$—$R^0$; O—S(=O)$_2$OH; O—S(=O)$_2$$OR^0$; O—S(=O)$_2$$NH_2$; O—S(=O)$_2$$NHR^0$; O—S(=O)$_2$N($R^0$)$_2$; $NH_2$; NH—$R^0$; N($R^0$)$_2$; NH—C(=O)—$R^0$; NH—C(=O)—O—$R^0$; NH—C(=O)—$NH_2$; NH—C(=O)—NH—$R^0$; NH—C(=O)—N($R^0$)$_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—N($R^0$)$_2$; NH—S(=O)$_2$OH; NH—S(=O)$_2$$R^0$; NH—S(=O)$_2$$OR^0$; NH—S(=O)$_2$$NH_2$; NH—S(=O)$_2$$NHR^0$; NH—S(=O)$_2$N(R)$_2$; $NR^0$—S(=O)$_2$OH; $NR^0$—S(=O)$_2$$R^0$; $NR^0$—S(=O)$_2$$OR^0$; $NR^0$—S(=O)$_2$$NH_2$; $NR^0$—S(=O)$_2$$NHR^0$; $NR^0$—S(=O)$_2$N($R^0$)$_2$; SH; $SR^0$; S(=O)$R^0$; S(=O)$_2$$R^0$; S(=O)$_2$OH; S(=O)$_2$$OR^0$; S(=O)$_2$$NH_2$; S(=O)$_2$$NHR^0$; or S(=O)$_2$N(R)$_2$;

$R^7$, $R^8$, $R^9$, $R^{19}$ mutually independently stand for H; F; Cl; Br; $C_{1-10}$ alkyl, saturated or unsaturated, branched or unbranched, unsubstituted or mono- or polysubstituted;

$R^{11}$ stands for H; F; Cl; Br; CN; $R^0$;

$R^{12}$ stands for H; F; Cl; Br; CN; or $C_{1-10}$ alkyl, saturated or unsaturated, branched or unbranched, unsubstituted or mono- or polysubstituted;

$R^{13}$ stands for H; F; Cl; Br; CN; $C_{1-10}$ alkyl or $C_{2-10}$ heteroalkyl, each saturated or unsaturated, branched or unbranched, unsubstituted or mono- or polysubstituted; $C_{3-7}$ cycloalkyl or heterocyclyl, each saturated or unsaturated, unsubstituted or mono- or polysubstituted; aryl or heteroaryl, each unsubstituted or mono- or polysubstituted; $C_{1-8}$ alkyl-bridged $C_{3-7}$ cycloalkyl or heterocyclyl, each saturated or unsaturated, unsubstituted or mono- or polysubstituted, wherein the alkyl chain can in each case be branched or unbranched, saturated or unsaturated, unsubstituted, mono- or polysubstituted; or $C_{2-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted;

$R^{14}$ stands for H; F; Cl; Br; CN; or $C_{1-10}$ alkyl, saturated or unsaturated, branched or unbranched, unsubstituted or mono- or polysubstituted;

or $R^{11}$ and $R^{13}$ together with the carbon atoms binding them as ring members form a $C_{3-7}$ cycloalkyl or heterocyclyl, each saturated or unsaturated, unsubstituted or mono- or polysubstituted, optionally fused to (hetero)aryl, unsubstituted or mono- or polysubstituted;

or $R^{11}$ and $R^{12}$; or $R^{13}$ and $R^{14}$, together with the carbon atoms binding them as ring members form a $C_{3-7}$ cycloalkyl or heterocyclyl, each saturated or unsaturated, unsubstituted or mono- or polysubstituted, each optionally fused to (hetero)aryl, unsubstituted or mono- or polysubstituted;

$R^{15}$ stands for $R^0$;

wherein "alkyl-substituted", "heteroalkyl-substituted", "heterocyclyl-substituted" and "cycloalkyl-substituted" stand for the substitution of one or more hydrogen atoms, each mutually independently, with F; Cl; Br; I; CN; $CF_3$; =O; =NH; =C($NH_2$)$_2$; $NO_2$; $R^0$; C(=O)H; C(=O)$R^0$; $CO_2H$; C(=O)$OR^0$; $CONH_2$; C(=O)$NHR^0$; C(=O)N($R^0$)$_2$; OH; $OR^0$; O—($C_{1-8}$ alkyl)-O; O—C(=O)—$R^0$; O—C(=O)—O—$R^0$; O—(C=O)—NH—$R^0$; O—C(=O)—N(R)$_2$; O—S(=O)$_2$—$R^0$; O—S(=O)$_2$OH; O—S(=O)$_2$$OR^0$; O—S(=O)$_2$$NH_2$; O—S(=O)$_2$$NHR^0$; O—S(=O)$_2$N($R^0$)$_2$; $NH_2$; NH—$R^0$; N($R^0$)$_2$; NH—C(=O)—$R^0$; NH—C(=O)—O—$R^0$; NH—C(=O)—$NH_2$; NH—C(=O)—NH—$R^0$; NH—C(=O)—N($R^0$)$_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—N($R^0$)$_2$; NH—S(=O)$_2$OH; NH—S(=O)$_2$$R^0$; NH—S(=O)$_2$$OR^0$; NH—S(=O)$_2$$NH_2$; NH—S(=O)$_2$$NHR^0$; NH—S(=O)$_2$N(R)$_2$; $NR^0$—S(=O)$_2$OH; $NR^0$—S(=O)$_2$$R^0$; $NR^0$—S(=O)$_2$$OR^0$; $NR^0$—S(=O)$_2$$NH_2$; $NR^0$—S(=O)$_2$$NHR^0$; $NR^0$—S(=O)$_2$N($R^0$)$_2$; SH; $SR^0$; S(=O)$R^0$; S(=O)$_2$$R^0$; S(=O)$_2$OH; S(=O)$_2$$OR^0$; S(=O)$_2$$NH_2$; S(=O)$_2$$NHR^0$; S(=O)$_2$N($R^0$)$_2$;

wherein "aryl-substituted" and "heteroaryl-substituted" stand for the substitution of one or more hydrogen atoms, each mutually independently, with F; Cl; Br; I; $NO_2$; $CF_3$; CN; $R^0$; C(=O)H; C(=O)$R^0$; $CO_2H$; C(=O)$OR^0$; $CONH_2$; C(=O)$NHR^0$; C(=O)N($R^0$)$_2$; OH; $OR^0$; O—($C_{1-8}$ alkyl)-O;

O—C(=O)—R°; O—C(=O)—O—R°; O—(C=O)—NH—R°; O—C(=O)—N(R°)$_2$; O—S(=O)$_2$—R°; O—S(=O)$_2$OH; O—S(=O)$_2$OR°; O—S(=O)$_2$NH$_2$; O—S(=O)$_2$NHR°; O—S(=O)$_2$N(R°)$_2$; NH$_2$; NH—R°; N(R°)$_2$; NH—C(=O)—R°; NH—C(=O)—O—R°; NH—C(=O)—NH$_2$; NH—C(=O)—NH—R°; NH—C(=O)—N(R°)$_2$; NR°—C(=O)—R°; NR°—C(=O)—O—R°; NR°—C(=O)—NH$_2$; NR°—C(=O)—NH—R°; NR°—C(=O)—N(R°)$_2$; NH—S(=O)$_2$OH; NH—S(=O)$_2$R°; NH—S(=O)$_2$OR°; NH—S(=O)$_2$NH$_2$; NH—S(=O)$_2$NHR°; NH—S(=O)$_2$N(R°)$_2$; NR°—S(=O)$_2$OH; NR°—S(=O)$_2$R°; NR°—S(=O)$_2$OR°; NR°—S(=O)$_2$NH$_2$; NR°—S(=O)$_2$NHR°; NR°—S(=O)$_2$N(R°)$_2$; SH; SR°; S(=O)R°; S(=O)$_2$R°; S(=O)$_2$OH; S(=O)$_2$OR°; S(=O)$_2$NH$_2$; S(=O)$_2$NHR°; S(=O)$_2$N(R°)$_2$;

in the form of the free compounds or salts of physiologically compatible acids or bases.

Within the meaning of this invention the expressions "$C_{1-2}$ alkyl", "$C_{1-4}$ alkyl", "$C_{1-6}$ alkyl", "$C_{1-8}$ alkyl", "$C_{1-10}$ alkyl", "$C_{2-4}$ alkyl" and "$C_{2-8}$ alkyl" include acyclic saturated or unsaturated hydrocarbon radicals, which can be branched or unbranched and unsubstituted or mono- or polysubstituted, having 1 to 2 or 1 to 4 or 1 to 8 or 1 to 10 or 2 to 4 or 2 to 8 C atoms respectively, i.e. $C_{1-2}$ alkanyls and $C_{1-2}$ alkenyls or $C_{1-4}$ alkanyls, $C_{1-4}$ alkenyls and $C_{2-4}$ alkynyls or $C_{1-8}$ alkanyls, $C_{1-8}$ alkenyls and $C_{2-8}$ alkynyls or $C_{1-10}$ alkanyls, $C_{1-10}$ alkenyls and $C_{2-10}$ alkynyls or $C_{2-4}$ alkanyls, $C_{2-4}$-alkenyls and $C_{2-4}$ alkynyls or $C_{2-8}$ alkanyls, $C_{2-8}$ alkenyls and $C_{2-8}$ alkynyls. Alkenyls have at least one C—C double bond and alkynyls have at least one C—C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethylenyl (vinyl), ethynyl, propenyl (—CH$_2$CH=CH$_2$, —CH=CH—CH$_3$, —C(=CH$_2$)—CH$_3$), propynyl (—CH—C≡CH, —C≡C—CH$_3$), butenyl, butynyl, pentenyl, pentynyl, hexenyl and hexynyl, heptenyl, heptynyl, octenyl, octynyl, nonenyl, nonynyl, decenyl and decynyl.

Within the meaning of this invention the expression "$C_{2-10}$ heteroalkyl" includes acyclic saturated or unsaturated hydrocarbon radicals having 2 to 10 C atoms, i.e. $C_{2-10}$ heteroalkanyls, $C_{2-10}$ heteroalkenyls and $C_{2-10}$ heteroalkynyls, each of which can be branched or unbranched and unsubstituted or mono- or polysubstituted and in which one, two or three carbon atoms are replaced by a heteroatom or a heteroatom group, each mutually independently selected from the group consisting of O, N, NH, N($C_{1-4}$ alkyl), preferably N(CH$_3$), S, S(=O) and S(=O)$_2$, wherein both the initial and also the terminal carbon atom of a $C_{2-10}$ heteroalkyls cannot be replaced by a heteroatom or a heteroatom group and adjacent carbon atoms cannot simultaneously be replaced by a heteroatom or a heteroatom group. One, two or three carbon atoms of a $C_{2-10}$ heteroalkyl are preferably replaced by a heteroatom or a heteroatom group, each mutually independently selected from the group consisting of O, N and S. Furthermore each heteroatom or each heteroatom group must have at least two carbon atoms as binding partners. $C_{2-10}$ heteroalkenyls have at least one C—C or one C—N double bond and $C_{2-10}$ heteroalkynyls have at least one C—C triple bond. $C_{2-10}$ heteroalkyl is preferably selected from the group consisting of —CH$_2$—O—CH$_3$, —CH$_2$—CH$_2$—O—CH$_3$, —CH$_2$—CH$_2$—O—CH$_2$—CH$_3$, —CH$_2$—CH$_2$—O—CH$_2$—CH$_2$—O—CH$_3$, —CH$_2$—NH—CH$_3$, —CH$_2$—CH$_2$—NH—CH$_3$, —CH$_2$—CH$_2$—NH—CH$_2$—CH$_3$, —CH$_2$—CH$_2$—NH—CH$_2$—CH$_2$—NH—CH$_3$, —CH$_2$—N(CH$_3$)—CH$_3$, —CH$_2$—N(CH$_3$)—CH$_2$—CH$_3$, —CH$_2$—CH$_2$—N(CH$_3$)—CH$_3$, —CH$_2$—CH$_2$—N(CH$_3$)—CH$_3$, —CH$_2$—S—CH$_3$, —CH$_2$—CH$_2$—S—CH$_2$—CH$_3$, —CH$_2$—CH$_2$—S—CH$_2$—CH$_2$—S—CH$_3$, —CH$_2$—CH$_2$—NH—CH$_2$—CH$_2$—O—CH$_3$ and —CH$_2$=N(CH$_3$).

For the purposes of this invention the expression "cycloalkyl", "$C_{3-7}$ cycloalkyl" or "$C_{3-6}$ cycloalkyl" denotes cyclic hydrocarbons having 3, 4, 5, 6 or optionally 7 carbon atoms, wherein the hydrocarbons can be saturated or unsaturated (but not aromatic), unsubstituted or mono- or polysubstituted. The binding of the cycloalkyl to the higher-order general structure can be made via any desired and possible ring member of the cycloalkyl radical. The cycloalkyl radicals can also be fused to further saturated, (partially) unsaturated, heterocyclic, aromatic or heteroaromatic ring systems, which can in turn be unsubstituted or mono- or polysubstituted. The cycloalkyl radicals can further be singly or multiply bridged, as for example in the case of adamantyl or dicyclopentadienyl. $C_{3-7}$ cycloalkyl is preferably selected from the group including cyclopropyl, cyclobutyl, cyclopentyl, cyclohexyl, cycloheptyl, cyclopentenyl, cyclohexenyl and cycloheptenyl.

The term "heterocyclyl" includes saturated or unsaturated (but not aromatic) cycloalkyls having three to seven ring members, in which one, two or three carbon atoms can be replaced by a heteroatom, each mutually independently selected from the group S, N or O, wherein the ring members can be unsubstituted or mono- or polysubstituted. The binding of the heterocyclyl to the higher-order general structure can be made via any desired and possible ring member of the heterocyclyl radical. The heterocyclyl radicals can also be fused to further saturated, (partially) unsaturated or aromatic or heteroaromatic ring systems, which can in turn be unsubstituted or mono- or polysubstituted. Heterocyclyl radicals from the group comprising azetidinyl, aziridinyl, azepanyl, quinolinyl, dioxanyl, dioxolanyl, furanyl, imidazolidinyl, isoxazolidinyl, isoquinolinyl, indolinyl, morpholinyl, pyranyl, pyrrolyl, pyridinyl, pyrrolyl, pyrrolidinyl, piperazinyl, piperidinyl, pyrazolidinyl, pyrazolinonyl or thiomorpholinyl are preferred.

Within the meaning of this invention, the term "aryl" denotes aromatic hydrocarbons having up to 14 ring members, inter alia phenyls and naphthyls. Each aryl radical can be present in unsubstituted or mono- or polysubstituted form, wherein the aryl substituents can be identical or different and can be at any desired and possible position of the aryl. The binding of the aryl to the higher-order general structure can be made via any desired and possible ring member of the aryl radical. The aryl radicals can also be fused to further saturated, (partially) unsaturated, heterocyclic, aromatic or heteroaromatic ring systems, which can in turn be unsubstituted or mono- or polysubstituted. Aryl is preferably selected from the group including phenyl, 1-naphthyl and 2-naphthyl, each of which can be unsubstituted or mono- or polysubstituted. A particularly preferred aryl is phenyl, unsubstituted or mono- or polysubstituted.

The term "heteroaryl" stands for a 5-, 6- or 7-membered cyclic aromatic radical containing at least 1, optionally also 2, 3, 4 or 5 heteroatoms, wherein the heteroatoms can each be mutually independently selected from the group S, N or O and the heteroaryl radical can be unsubstituted or mono- or polysubstituted; if the heteroaryl is substituted, the substituents can be identical or different and can be at any desired and possible position of the heteroaryl. Preferred heteroatoms are S, N and O, S and N are particularly preferred. The binding to the higher-order general structure can be made via any desired and possible ring member of the heteroaryl radical. The heteroaryl can also be part of a bicyclic or polycyclic system having up to 14 ring members, wherein the ring system can be formed with further saturated, (partially) unsaturated, heterocyclic or aromatic or heteroaromatic rings, which can in turn be unsubstituted or mono- or polysubstituted. The heteroaryl radical is preferably selected from the group comprising benzofuranyl, benzoimidazolyl, benzothienyl, benzothiadiazolyl, benzothiazolyl, benzotriazolyl, benzodioxolanyl, benzodioxanyl, quinazolinyl, carbazolyl, quinolinyl, furyl (furanyl), imidazolyl, indazolyl, indolizinyl, indolyl, isoquinolinyl, isoxazoyl, isothiazolyl, indolyl, oxadiazolyl, phthalazinyl, pyrazolyl, pyridyl, pyrrolyl, pyridazinyl, pyrimidinyl, pyrazinyl, purinyl, phenazinyl, thienyl, triazolyl, thiazolyl, thiadiazolyl or triazinyl. Pyridyl, thienyl, indolyl and indazolyl are particularly preferred.

Within the meaning of the invention the expressions "$C_{1-2}$ alkyl- or $C_{1-4}$ alkyl- or $C_{1-8}$ alkyl- or $C_{2-8}$ alkyl-bridged aryl, heteroaryl, heterocyclyl or cycloalkyl" mean that $C_{1-2}$ alkyl or $C_{1-4}$ alkyl or $C_{1-8}$ alkyl or $C_{2-8}$ alkyl and aryl or heteroaryl or heterocyclyl or cycloalkyl have the meanings defined above and the aryl or heteroaryl or heterocyclyl or cycloalkyl radical is bound by a $C_{1-2}$ alkyl or a $C_{1-4}$ alkyl or a $C_{1-8}$ alkyl or a $C_{2-8}$ alkyl group to the higher-order general structure. The alkyl chain can in all cases be saturated or unsaturated, branched or unbranched, unsubstituted or mono- or polysubstituted.

In connection with "alkyl", "heteroalkyl", "heterocyclyl" and "cycloalkyl" the term "mono- or polysubstituted" within the meaning of this invention is understood to mean the single or multiple, e.g. two, three or four times, substitution of one or more hydrogen atoms each mutually independently with substituents selected from the group comprising F; Cl; Br; I; CN; $CF_3$; =O; =NH; =C(NH$_2$)$_2$; NO$_2$; $R^0$; C(=O)H; C(=O)$R^0$; CO$_2$H; C(=O)O$R^0$; CONH$_2$; C(=O)NH$R^0$; C(=O)N($R^0$)$_2$; OH; O$R^0$; —O—($C_{1-8}$ alkyl)-O—; O—C(=O)—$R^0$; O—C(=O)—O—$R^0$; O—(C=O)—NH—$R^0$; O—C(=O)—N($R^0$)$_2$; O—S(=O)$_2$—$R^0$; O—S(=O)$_2$OH; O—S(=O)$_2$O$R^0$; O—S(=O)$_2$NH$_2$; O—S(=O)$_2$NH$R^0$; O—S(=O)$_2$N($R^0$)$_2$; NH$_2$; NH—$R^0$; N($R^0$)$_2$; NH—C(=O)—$R^0$; NH—C(=O)—O—$R^0$; NH—C(=O)—NH$_2$; NH—C(=O)—NH—$R^0$; NH—C(=O)—N($R^0$)$_2$; N$R^0$—C(=O)—$R^0$; N$R^0$—C(=O)—O—$R^0$; N$R^0$—C(=O)—NH$_2$; N$R^0$—C(=O)—NH—$R^0$; N$R^0$—C(=O)—N(R)$_2$; NH—S(=O)$_2$OH; NH—S(=O)$_2$$R^0$; NH—S(=O)$_2$O$R^0$; NH—S(=O)$_2$NH$_2$; NH—S(=O)$_2$NH$R^0$; NH—S(=O)$_2$N($R^0$)$_2$; N$R^0$—S(=O)$_2$OH; N$R^0$—S(=O)$_2$$R^0$; N$R^0$—S(=O)$_2$O$R^0$; N$R^0$—S(=O)$_2$NH$_2$; N$R^0$—S(=O)$_2$NH$R^0$; N$R^0$—S(=O)$_2$N($R^0$)$_2$; SH; S$R^0$; S(=O)$R^0$; S(=O)$_2$$R^0$; S(=O)$_2$OH; S(=O)$_2$O$R^0$; S(=O)$_2$NH$_2$; S(=O)$_2$NH$R^0$; S(=O)$_2$N($R^0$)$_2$, wherein polysubstituted radicals are understood to be radicals which are substituted multiple times, for example twice, three or four times, at different or the same atoms, for example substituted three times at the same C atom, as in the case of $CF_3$ or $CH_2CF_3$, or at different points, as in the case of CH(OH)—CH=CH—CHCl$_2$. A substituent can in turn itself optionally be mono- or polysubstituted. The polysubstitution can be performed with identical or different substituents.

Preferred "alkyl", "heteroalkyl", "heterocyclyl" and "cycloalkyl" substituents are F; Cl; Br; I; NO$_2$; $CF_3$; CN; =O; =NH; $R^0$; C(=O)($R^0$ or H); C(=O)O($R^0$ or H); C(=O)N($R^0$ or H)$_2$; OH; O$R^0$; O—($C_{1-8}$ alkyl)-O—; O—($C_{1-8}$ alkyl)-O—$C_{1-8}$ alkyl; $OCF_3$; N($R^0$ or H)$_2$; N($R^0$ or H)—C(=O)—$R^0$; N($R^0$ or H)—C(=O)—N($R^0$ or H)$_2$; SH; $SCF_3$; S$R^0$; S(=O)$_2$$R^0$; S(=O)$_2$O($R^0$ or H); S(=O)$_2$—N($R^0$ or H)$_2$.

The expression "($R^0$ or H)" within a radical means that $R^0$ and H can occur within this radical in any possible combination. Thus the radical "N($R^0$ or H)$_2$" can stand for "NH$_2$", "NH$R^0$" and "N($R^0$)$_2$", for example. If $R^0$ occurs more than once within a radical, as in the case of "N($R^0$)$_2$", then $R^0$ can have the same or different meanings in each case: in the present example of "N($R^0$)$_2$", for example, $R^0$ can stand twice for aryl, giving the functional group "N(aryl)$_2$", or $R^0$ can stand once for aryl and once for $C_{1-10}$ alkyl, giving the functional group "N(aryl)($C_{1-10}$ alkyl)".

In connection with "aryl" and "heteroaryl" the expression "mono- or polysubstituted" within the meaning of this invention is understood to mean the single or multiple, e.g. two, three or four times, substitution of one or more hydrogen atoms in the ring system, each mutually independently with substituents selected from the group comprising F; Cl; Br; I; NO$_2$; $CF_3$; CN; $R^0$; C(=O)H; C(=O)$R^0$; CO$_2$H; C(=O)O$R^0$; CONH$_2$; C(=O)NH$R^0$; C(=O)N($R^0$)$_2$; OH; O$R^0$; O—($C_{1-8}$ alkyl)-O—; O—C(=O)—$R^0$; O—C(=O)—O—$R^0$; O—(C=O)—NH—$R^0$; O—C(=O)—N($R^0$)$_2$; O—S(=O)$_2$—$R^0$; O—S(=O)$_2$OH; O—S(=O)$_2$O$R^0$; O—S(=O)$_2$NH$_2$; O—S(=O)$_2$NH$R^0$; O—S(=O)$_2$N($R^0$)$_2$; NH$_2$; NH—$R^0$; N($R^0$)$_2$; NH—C(=O)—$R^0$; NH—C(=O)—O—$R^0$; NH—C(=O)—NH$_2$; NH—C(=O)—NH—$R^0$; NH—C(=O)—N($R^0$)$_2$; N$R^0$—C(=O)—$R^0$; N$R^0$—C(=O)—O—$R^0$; N$R^0$—C(=O)—NH$_2$; N$R^0$—C(=O)—NH—$R^0$; N$R^0$—C(=O)—N($R^0$)$_2$; NH—S(=O)$_2$OH; NH—S(=O)$_2$$R^0$; NH—S(=O)$_2$O$R^0$; NH—S(=O)$_2$NH$_2$; NH—S(=O)$_2$NH$R^0$; NH—S(=O)$_2$N($R^0$)$_2$; N$R^0$—S(=O)$_2$OH; N$R^0$—S(=O)$_2$$R^0$; N$R^0$—S(=O)$_2$O$R^0$; N$R^0$—S(=O)$_2$NH$_2$; N$R^0$—S(=O)$_2$NH$R^0$; N$R^0$—S(=O)$_2$N($R^0$)$_2$; SH; S$R^0$; S(=O)$R^0$; S(=O)$_2$$R^0$; S(=O)$_2$OH; S(=O)$_2$O$R^0$; S(=O)$_2$NH$_2$; S(=O)$_2$NH$R^0$; S(=O)$_2$N($R^0$)$_2$, at one or optionally different atoms, wherein a substituent can in turn itself optionally be mono- or polysubstituted. The polysubstitution is performed with identical or with different substituents.

Preferred "aryl" and "heteroaryl" substituents are F; Cl; Br; I; NO$_2$; $CF_3$; CN; $R^0$; C(=O)($R^0$ or H); C(=O)O($R^0$ or H); C(=O)N($R^0$ or H)$_2$; OH; O$R^0$; —O—($C_{1-8}$ alkyl)-O—; O—($C_{1-8}$ alkyl)-O—$C_{1-8}$ alkyl; $OCF_3$; N($R^0$ or H)$_2$; N($R^0$ or H)—C(=O)—$R^0$; N($R^0$ or H)—C(=O)—N($R^0$ or H)$_2$; SH; $SCF_3$; S$R^0$; S(=O)$_2$$R^0$; S(=O)$_2$O($R^0$ or H); S(=O)$_2$—N($R^0$ or H)$_2$.

The compounds according to the invention are defined by substituents, for example by $R^1$, $R^2$ and $R^3$ (1$^{st}$ generation substituents), which are in turn optionally substituted (2$^{nd}$ generation substituents). Depending on the definition, these substituents of the substituents can themselves be substituted again (3$^{rd}$ generation substituents). For example, if $R^3$=$R^0$ where $R^0$=aryl (1$^{st}$ generation substituent), then aryl can itself be substituted, e.g. with NH$R^0$, where $R^0$=$C_{1-10}$ alkyl (2$^{nd}$ generation substituent). This gives the functional group aryl-NH$C_{1-10}$ alkyl. $C_{1-10}$ alkyl can then itself be substituted again, for example with Cl (3$^{rd}$ generation substituent). This then gives in total the functional group aryl-NH$C_{1-10}$ alkyl-Cl.

In a preferred embodiment the 3$^{rd}$ generation substituents cannot, however, be substituted again, i.e. there are then no 4$^{th}$ generation substituents.

In another preferred embodiment the 2$^{nd}$ generation substituents cannot be substituted again, i.e. there are then no 3$^{rd}$ generation substituents either. In other words, in this embodiment the functional groups for $R^0$ to $R^{23}$ can each optionally be substituted, but the various substituents cannot then themselves be substituted again.

If a radical occurs more than once within a molecule, such as the radical $R^0$ for example, then this radical can have different meanings for different substituents: for example, if both $R^{11}$=$R^0$ and $R^{15}$=$R^0$, then for $R^{11}$ $R^0$ can denote aryl and for $R^{15}$ $R^0$ can denote $C_{1-10}$ alkyl.

In some cases the compounds according to the invention are defined by substituents which together with the carbon atom(s) or heteroatom(s) binding them as ring member or ring members form a ring, for example a $C_{3-7}$ cycloalkyl or a heterocyclyl, each saturated or unsaturated, unsubstituted or mono- or polysubstituted. These ring systems thus formed can optionally be fused to (hetero)aryl, i.e. to an aryl such as phenyl or a heteroaryl such as pyridyl, wherein the (hetero) aryl radical can be unsubstituted or mono- or polysubstituted. The ring systems thus formed are preferably fused to an aryl, particularly preferably to phenyl. If the substituents $R^{11}$ and $R^{13}$, for example, form a cyclohexyl ring with the carbon atoms binding them, then this cyclohexyl ring can be fused to phenyl to form tetrahydronaphthyl.

Within the meaning of this invention the term "salt formed with a physiologically compatible acid" is understood to mean salts of the individual active ingredient with inorganic or organic acids which are physiologically—particularly when used in humans and/or mammals—compatible. Hydrochloride is particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, saccharinic acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. Citric acid and hydrochloric acid are particularly preferred.

Physiologically compatible salts with cations or bases are salts of the individual compound as anion with at least one, preferably inorganic, cation, which are physiologically—particularly when used in humans and/or mammals—compatible. Particularly preferred are the salts of the alkali and alkaline-earth metals, but also ammonium salts, but in particular (mono) or (di)sodium, (mono) or (di)potassium, magnesium or calcium salts.

In a preferred embodiment the substituent $R^1$ is selected from the group consisting of $C_{1-10}$ alkyl, preferably $C_{1-6}$ alkyl, or $C_{2-10}$ heteroalkyl, each saturated or unsaturated, branched or unbranched, unsubstituted or mono- or polysubstituted; $C_{3-7}$ cycloalkyl, preferably $C_{3-6}$ cycloalkyl, each saturated or unsaturated, unsubstituted or mono- or polysubstituted; aryl or heteroaryl, each unsubstituted or mono- or polysubstituted; $C_{1-8}$ alkyl-bridged $C_{3-7}$ cycloalkyl, preferably $C_{3-6}$ cycloalkyl, each saturated or unsaturated, unsubstituted or mono- or polysubstituted, wherein the alkyl chain can be branched or unbranched, saturated or unsaturated, unsubstituted, mono- or polysubstituted; $C_{1-8}$ alkyl-bridged heteroaryl, unsubstituted or mono- or polysubstituted, wherein the alkyl chain can be branched or unbranched, saturated or unsaturated, unsubstituted, mono- or polysubstituted; or $C_{1-8}$ alkyl-bridged aryl, unsubstituted or mono- or polysubstituted, wherein the alkyl chain can be unbranched, saturated or unsaturated, unsubstituted;
and the substituent $R^2$ is selected from the group consisting of H or $C_{1-10}$ alkyl, saturated or unsaturated, branched or unbranched, unsubstituted or mono- or polysubstituted.

In a further preferred embodiment the substituent $R^1$ is selected from the group consisting of $C_{1-10}$ alkyl, saturated or unsaturated, branched or unbranched, unsubstituted; $C_{3-7}$ cycloalkyl, saturated or unsaturated, unsubstituted or mono- or polysubstituted; phenyl, thienyl or pyridyl, each unsubstituted or mono- or polysubstituted; $C_{1-4}$ alkyl-bridged $C_{3-7}$ cycloalkyl, saturated or unsaturated, unsubstituted or mono- or polysubstituted, wherein the alkyl chain can be branched or unbranched, saturated or unsaturated, unsubstituted; $C_{1-4}$ alkyl-bridged thienyl or pyridyl, each unsubstituted or mono- or polysubstituted, wherein the alkyl chain can be branched or unbranched, saturated or unsaturated, unsubstituted, mono- or polysubstituted; or $C_{1-4}$ alkyl-bridged phenyl, unsubstituted or mono- or polysubstituted, wherein the alkyl chain can be unbranched, saturated or unsaturated, unsubstituted;
and the substituent $R^2$ is selected from the group consisting of H or $C_{1-10}$ alkyl, saturated or unsaturated, branched or unbranched, unsubstituted.

In a further preferred embodiment the substituent $R^1$ is selected from the group consisting of
$C_{1-10}$ alkyl, saturated, branched or unbranched, unsubstituted; or
in accordance with the general formula (Ia) below denotes $(CH_2)_e$-bridged phenyl,

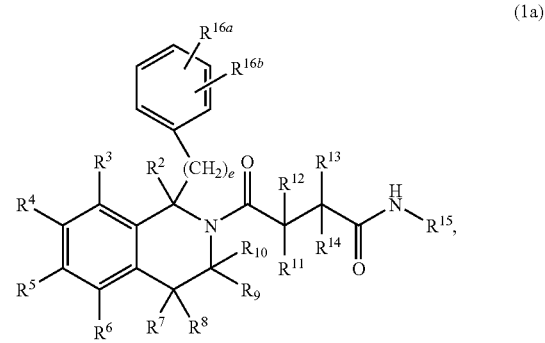

(1a)

mono- or disubstituted with $R^{16a}$ and/or $R^{16b}$;
or in accordance with the general formula (Ib) below denotes $(CH_2)_e$-bridged thienyl,

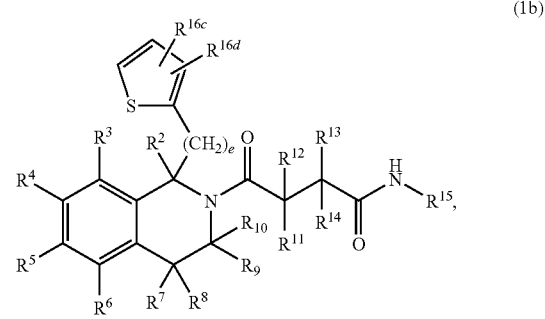

(1b)

mono- or disubstituted with $R^{16c}$ and/or $R^{16d}$;
or in accordance with the general formula (Ic) below denotes $(CH_2)_e$-bridged pyridyl,

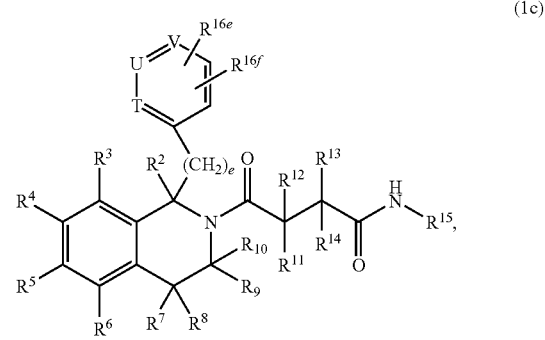

(1c)

mono- or disubstituted with $R^{16e}$ and/or $R^{16f}$;

wherein just one of the substituents T, U and V stands for N and the remaining substituents in each case denote CH; or in accordance with the general formula (Id) below denotes $(CH_2)_e$-bridged $C_{3-7}$ cycloalkyl,

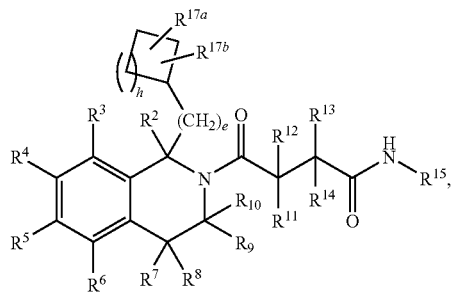

(1d)

mono- or disubstituted with $R^{17a}$ and/or $R^{17b}$;
wherein h denotes 0, 1, 2, 3 or 4, preferably stands for 0; and the substituent $R^2$ stands in each case for H;
wherein e stands in each case for 0, 1, 2, 3 or 4, preferably for 0;
$R^{16a}$, $R^{16b}$, $R^{16c}$, $R^{16d}$, $R^{16e}$ and $R^{16f}$ are each mutually independently selected from the group consisting of H, F, Cl, Br, CN, $NH_2$, $OCF_3$, $SCF_3$, $CF_3$, $C_{1-8}$ alkyl or O—$C_{1-8}$ alkyl, each saturated or unsaturated, branched or unbranched, unsubstituted or mono- or polysubstituted; aryl, heteroaryl, each unsubstituted or mono- or polysubstituted;
$R^{17a}$ and $R^{17b}$ are mutually independently selected from the group consisting of H, F, Cl, Br, CN, $NH_2$, $OCF_3$, $SCF_3$, $CF_3$, $C_{1-8}$ alkyl or O—$C_{1-8}$ alkyl, each saturated or unsaturated, branched or unbranched, unsubstituted or mono- or polysubstituted; aryl, heteroaryl, each unsubstituted or mono- or polysubstituted.
$R^{16a}$ and $R^{16b}$ are preferably mutually independently selected from the group consisting of H, F, Cl, $CH_3$, $OCH_3$ and $CF_3$; $R^{16a}$ and $R^{16b}$ particularly preferably each stand for H.
$R^{16c}$ and $R^{16d}$ are preferably mutually independently selected from the group consisting of H, F, Cl, $CH_3$, $OCH_3$ and $CF_3$; $R^{16c}$ and $R^{16d}$ particularly preferably each stand for H.
$R^{16e}$ and $R^{16f}$ are preferably mutually independently selected from the group consisting of H, F, Cl, $CH_3$, $OCH_3$ and $CF_3$; $R^{16e}$ and $R^{16f}$ particularly preferably each stand for H.
h preferably stands for 2 or 3, particularly preferably for 3.
$R^{17a}$ and $R^{17b}$ are preferably mutually independently selected from the group consisting of H, F, Cl, Br, $CH_3$, $OCH_3$ and $CF_3$; $R^{17a}$ and $R^{17b}$ particularly preferably each stand for H.
Compounds having the formulae (1a) and (1b) are most particularly preferred.
In a further preferred embodiment the substituent $R^1$ is selected from the group consisting of $C_{1-6}$ alkyl or $C_{3-6}$ cycloalkyl, each saturated, branched or unbranched, unsubstituted.
In a further preferred embodiment the substituents $R^3$, $R^4$, $R^5$ and $R^6$ are mutually independently selected from the group consisting of H; F; Cl; Br; I; $NO_2$; $CF_3$; CN; $R^0$; C(=O)($R^0$ or H); C(=O)O($R^0$ or H); C(=O)N($R^0$ or H)$_2$; OH; $OR^0$; O—($C_{1-8}$ alkyl)-O; O—($C_{1-8}$ alkyl)-O—$C_{1-8}$ alkyl; $OCF_3$; N($R^0$ or H)$_2$; N($R^0$ or H)—C(=O)—$R^0$; N($R^0$ or H)—C(=O)—N($R^0$ or H)$_2$; SH; $SCF_3$; $SR^0$; S(=O)$_2R^0$; S(=O)$_2$O($R^0$ or H); S(=O)$_2$—N($R^0$ or H)$_2$.
The substituents $R^3$, $R^4$, $R^5$ and $R^6$ are preferably mutually independently selected from the group consisting of H; F; Cl; Br; I; $NO_2$; $CF_3$; CN; $NH_2$; NH—$C_{1-8}$ alkyl; N($C_{1-8}$ alkyl)$_2$; NH—C(=O)$C_{1-8}$ alkyl; NH—C(=O) aryl; NH—C(=O) heteroaryl; $C_{1-8}$ alkyl; $CF_3$; CHO; C(=O)$C_{1-8}$ alkyl; C(=O) aryl; C(=O) heteroaryl; $CO_2H$; C(=O)O—$C_{1-8}$ alkyl; C(=O)O aryl; C(=O)O heteroaryl; $CONH_2$; C(=O)NH—$C_{1-8}$ alkyl; C(=O)N($C_{1-8}$ alkyl)$_2$; C(=O)NH aryl; C(=O)N (aryl)$_2$; C(=O)NH heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O-$C_{1-8}$ alkyl; $OCF_3$; O—($C_{1-8}$ alkyl)-O; O—($C_{1-8}$ alkyl)-O—$C_{1-8}$ alkyl; O-benzyl; O-aryl; O-heteroaryl; O—C(=O)$C_{1-8}$-alkyl; O—C(=O)aryl; O—C(=O)heteroaryl; SH; S—$C_{1-8}$ alkyl; $SCF_3$; S-benzyl; S-aryl; S-heteroaryl; aryl; heteroaryl; $C_{3-7}$ cycloalkyl; heterocyclyl or $C_{1-8}$ alkyl-bridged aryl, heteroaryl, $C_{3-7}$ cycloalkyl or heterocyclyl.
The substituents $R^3$, $R^4$, $R^5$ and $R^6$ are particularly preferably each mutually independently selected from the group consisting of H; F; Cl; Br; CN; $CF_3$; $NH_2$; $OCF_3$; $SCF_3$; $C_{1-8}$ alkyl; O—$C_{1-8}$ alkyl; NH($C_{1-8}$ alkyl); N($C_{1-8}$ alkyl)$_2$; OH; and SH.
The substituents $R^3$, $R^4$, $R^5$ and $R^6$ are most particularly preferably each mutually independently selected from the group consisting of H; F; Cl; $OCH_3$; $CH_3$; $CF_3$ and $OCF_3$.
In particular $R^3$ and $R^5$ each stand for H and $R^4$ and $R^6$ are each mutually independently selected from the group consisting of H; F; $OCH_3$; $CH_3$ and $CF_3$.
In a further preferred embodiment the substituents $R^7$, $R^8$, $R^9$ and $R^{10}$ are each mutually independently selected from the group consisting of H, $C_{1-10}$ alkyl, saturated or unsaturated, branched or unbranched, unsubstituted or mono- or polysubstituted.
The substituents $R^7$, $R^8$, $R^9$ and $R^{10}$ are preferably mutually independently selected from the group consisting of H or $C_{1-10}$ alkyl, saturated, unbranched, unsubstituted.
The substituents $R^7$, $R^8$, $R^9$ and $R^{10}$ are particularly preferably mutually independently selected from the group consisting of H or $CH_3$.
In a further preferred embodiment the substituent $R^{11}$ is selected from the group consisting of H; F; Cl; Br; CN; $C_{1-10}$ alkyl, saturated or unsaturated, branched or unbranched, unsubstituted or mono- or polysubstituted; phenyl or heteroaryl, each unsubstituted or mono- or polysubstituted; $C_{1-4}$ alkyl-bridged phenyl or heteroaryl, each unsubstituted or mono- or polysubstituted, wherein the alkyl chain can in each case be branched or unbranched, saturated or unsaturated, unsubstituted or mono- or polysubstituted;
and $R^{13}$ is selected from the group consisting of H; F; Cl; Br; CN; $C_{1-10}$ alkyl, saturated or unsaturated, branched or unbranched, unsubstituted or mono- or polysubstituted; phenyl or heteroaryl, each unsubstituted or mono- or polysubstituted; $C_{2-4}$ alkyl-bridged phenyl or heteroaryl, each unsubstituted or mono- or polysubstituted, wherein the alkyl chain can in each case be branched or unbranched, saturated or unsaturated, unsubstituted or mono- or polysubstituted;
or $R^{11}$ and $R^{13}$ together with the carbon atoms binding them as ring members form a $C_{3-7}$ cycloalkyl or heterocyclyl, each saturated or unsaturated, unsubstituted or mono- or polysubstituted, optionally fused to phenyl, unsubstituted or mono- or polysubstituted.
$R^{11}$ is preferably selected from the group consisting of H; $C_{1-10}$ alkyl, saturated or unsaturated, branched or unbranched, unsubstituted; phenyl, unsubstituted or mono- or polysubstituted; $C_{1-4}$ alkyl-bridged phenyl, unsubstituted or mono- or polysubstituted, wherein the alkyl chain can be branched or unbranched, saturated or unsaturated, unsubstituted or mono- or polysubstituted;

and the radical $R^{13}$ can be selected from the group consisting of H; $C_{1-10}$ alkyl, saturated or unsaturated, branched or unbranched, unsubstituted; phenyl, unsubstituted or mono- or polysubstituted; $C_{2-4}$ alkyl-bridged phenyl, unsubstituted or mono- or polysubstituted, wherein the alkyl chain can in each case be branched or unbranched, saturated or unsaturated, unsubstituted or mono- or polysubstituted.

$R^{11}$ is particularly preferably selected from the group consisting of H; $C_{1-4}$ alkyl, saturated or unsaturated, branched or unbranched, unsubstituted; phenyl or benzyl, each unsubstituted or mono- or polysubstituted;

and the radical $R^{13}$ is selected from the group consisting of H; $C_{1-4}$ alkyl, saturated or unsaturated, branched or unbranched, unsubstituted; phenyl, unsubstituted or mono- or polysubstituted.

The radicals $R^{11}$ and $R^{13}$ are most particularly preferably each mutually independently selected from the group consisting of H and $CH_3$; in particular $R^{11}$ and $R^{13}$ each stand for H.

In a further preferred embodiment $R^{12}$ and $R^{14}$ are each mutually independently selected from the group consisting of H; $C_{1-10}$ alkyl, saturated or unsaturated, branched or unbranched, unsubstituted or mono- or polysubstituted.

$R^{12}$ and $R^{14}$ are preferably each mutually independently selected from the group consisting of H; $C_{1-4}$ alkyl, saturated or unsaturated, branched or unbranched, unsubstituted.

The radicals $R^{12}$ and $R^{14}$ are most particularly preferably each mutually independently selected from the group consisting of H and $CH_3$; in particular $R^{12}$ and $R^{14}$ each stand for H.

In a further preferred embodiment the substituent $R^{15}$ is selected from the group consisting of $C_{3-10}$ alkyl or $C_{2-10}$ heteroalkyl, each saturated or unsaturated; branched or unbranched, unsubstituted or mono- or polysubstituted; $C_{3-7}$ cycloalkyl, saturated or unsaturated, unsubstituted or mono- or polysubstituted; aryl or heteroaryl, unsubstituted or mono- or polysubstituted; $C_{1-8}$ alkyl-bridged $C_{3-7}$ cycloalkyl, saturated or unsaturated, unsubstituted or mono- or polysubstituted, wherein the alkyl chain can in each case be branched or unbranched, saturated or unsaturated, unsubstituted, mono- or polysubstituted; $C_{1-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted.

The substituent $R^{15}$ is preferably selected from the group consisting of $C_{3-10}$ alkyl or $C_{2-10}$ heteroalkyl, each saturated or unsaturated; branched or unbranched, unsubstituted or mono- or polysubstituted; $C_{3-7}$ cycloalkyl, saturated or unsaturated, unsubstituted or mono- or polysubstituted; aryl or heteroaryl, unsubstituted or mono- or polysubstituted; $C_{1-8}$ alkyl-bridged $C_{3-7}$ cycloalkyl, saturated or unsaturated, unsubstituted or mono- or polysubstituted, wherein the alkyl chain can in each case be branched or unbranched, saturated or unsaturated, unsubstituted, mono- or polysubstituted; $C_{1-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted; with the proviso that if $R^{15}$ denotes heteroaryl, the heteroaryl is bound by a carbon atom in the heteroaryl.

The radical $R^{15}$ particularly preferably stands for $C_{3-10}$ alkyl, saturated or unsaturated; branched or unbranched, unsubstituted or mono- or polysubstituted; or is selected from the following substructures A, B or C,

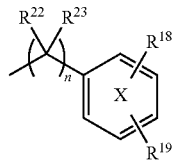

A

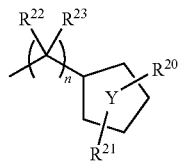

B

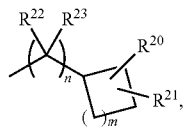

C wherein n=0, 1, 2, 3, 4, 5, 6, 7 or 8; particularly preferably stands for 0, 1, 2 or 3, in particular denotes 1;

m=0, 1, 2 or 3;

ring X can contain one or two N atoms as ring member(s);

ring Y contains at least 1 heteroatom selected from N, O or S and can contain up to 3 heteroatoms mutually independently selected from N, O or S; and/or can contain one or two double bonds;

$R^{18}$ and $R^{19}$ mutually independently denote H; F; Cl; Br; I; $NO_2$; $CF_3$; CN; $R^0$; C(=O)($R^0$ or H); C(=O)O($R^0$ or H); C(=O)N($R^0$ or H)$_2$; OH; OR$^0$; O—($C_{1-8}$ alkyl)-O; O—($C_{1-8}$ alkyl)-O—$C_{1-8}$ alkyl; N($R^0$ or H)$_2$; N($R^0$ or H)—C(=O)—$R^0$; N($R^0$ or H)—C(=O)—N($R^0$ or H)$_2$; SH; SR$^0$; S(=O)$_2R^0$; S(=O)$_2$O($R^0$ or H); S(=O)$_2$—N($R^0$ or H)$_2$H;

or $R^{18}$ and $R^{19}$ together with the carbon or nitrogen atoms binding them as ring members form an aryl or heteroaryl fused to the phenyl or heteroaryl ring, each unsubstituted or mono- or polysubstituted; or a $C_{3-7}$ cycloalkyl or heterocyclyl fused to the phenyl or heteroaryl ring, each saturated or unsaturated, unsubstituted or mono- or polysubstituted;

$R^{20}$ and $R^{21}$ mutually independently denote H or $C_{1-10}$ alkyl, saturated or unsaturated; branched or unbranched, unsubstituted or mono- or polysubstituted; $C_{3-7}$ cycloalkyl or heterocyclyl, each saturated or unsaturated, unsubstituted or mono- or polysubstituted;

or $R^{20}$ and $R^{21}$ together with the carbon atoms or heteroatoms binding them as ring members form an aryl or heteroaryl fused to ring Y, each unsubstituted or mono- or polysubstituted;

$R^{22}$ and $R^{23}$ mutually independently denote H; or $C_{1-10}$ alkyl, saturated or unsaturated; branched or unbranched, unsubstituted.

Compounds in which $R^{15}$ has the meaning of substructure A are particularly preferred.

In a further preferred embodiment the radical $R^{15}$ is selected from the following substructures A-a, B-a or C-a,

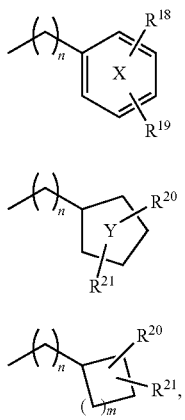

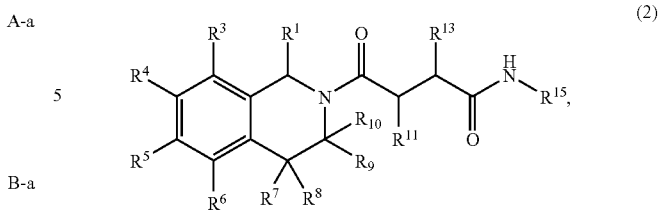

wherein n denotes 0, 1, 2 or 3, particularly preferably stands for 1;

m=0, 1, 2 or 3;

ring X can contain an N atom as ring member;

ring Y contains a heteroatom selected from N, O or S and/or contains one or two double bonds;

$R^{18}$ and $R^{19}$ mutually independently denote H; F; Cl; Br; I; $NO_2$; CN; $NH_2$; $C_{1-10}$ alkyl, saturated or unsaturated; branched or unbranched, unsubstituted; benzyl; $CF_3$; $NH(C_{1-10}$ alkyl); $N(C_{1-10}$ alkyl$)_2$; OH; O—$C_{1-10}$ alkyl; $OCF_3$; O—($C_{1-10}$ alkyl)-O; O-benzyl; SH; S—$C_{1-10}$ alkyl; $SCF_3$; S-benzyl; phenyl, unsubstituted or mono- or polysubstituted; or $R^{18}$ and $R^{19}$ together with the carbon or nitrogen atoms binding them as ring members form a phenyl or heteroaryl fused to the phenyl or heteroaryl ring, each unsubstituted or mono- or polysubstituted;

$R^{20}$ and $R^{21}$ together with the carbon atoms or heteroatoms binding them as ring members form a phenyl fused to ring Y, each unsubstituted or mono- or polysubstituted;

or $R^{20}$ and $R^{21}$ together with the carbon atoms or heteroatoms binding them as ring members form an aryl or heteroaryl fused to ring Y, each unsubstituted or mono- or polysubstituted.

$R^{22}$ and $R^{23}$ mutually independently denote H or $CH_3$, in particular $R^{22}$ and $R^{23}$ each stand for H.

Compounds in which $R^{15}$ has the meaning of substructure A-a are most particularly preferred, wherein n denotes 0, 1, 2 or 3, in particular 1;

ring X contains no N atom as ring member;

$R^{18}$ and $R^{19}$ mutually independently denote H; F; Cl; Br; CN; $NH_2$; $C_{1-4}$ alkyl; $CF_3$; OH; O—$C_{1-4}$ alkyl; $OCF_3$; or $SCF_3$; in particular $R^{18}$ and $R^{19}$ mutually independently denote H; F; Cl, $CH_3$, $OCH_3$ or $CF_3$;

or $R^{18}$ and $R^{19}$ together with the phenyl ring X form an indazolyl, unsubstituted or mono- or polysubstituted; or together with the carbon atoms of the phenyl ring X binding them as ring members form O—$CH_2$—O; or O—$CH_2$—$CH_2$—O.

A further preferred embodiment of the compounds according to the invention having the general formula (1) has the general formula (2)

wherein $R^1$ stands for $C_{1-10}$ alkyl, preferably $C_{1-6}$ alkyl, or $C_{2-10}$ heteroalkyl, each saturated or unsaturated, branched or unbranched, unsubstituted or mono- or polysubstituted; $C_{3-7}$ cycloalkyl, preferably $C_{3-6}$ cycloalkyl, each saturated or unsaturated, unsubstituted or mono- or polysubstituted; phenyl, thienyl or pyridyl, each unsubstituted or mono- or polysubstituted; $C_{1-8}$ alkyl-bridged $C_{3-7}$ cycloalkyl, saturated or unsaturated, unsubstituted or mono- or polysubstituted; $C_{1-8}$ alkyl-bridged phenyl, unsubstituted or mono- or polysubstituted, wherein the alkyl chain can be branched or unbranched, saturated or unsaturated, unsubstituted; or $C_{1-8}$ alkyl-bridged thienyl or pyridyl, unsubstituted or mono- or polysubstituted, wherein the alkyl chain can be branched or unbranched, saturated or unsaturated, unsubstituted or mono- or polysubstituted;

$R^3$, $R^4$, $R^5$ and $R^6$ each mutually independently denote H; F; Cl; Br; I; $NO_2$; $CF_3$; CN; $R^0$; C(=O)($R^0$ or H); C(=O)O($R^0$ or H); C(=O)N($R^0$ or H$)_2$; OH; $OR^0$; O—($C_{1-8}$ alkyl)-O; O—($C_{1-8}$ alkyl)-O—$C_{1-8}$ alkyl; N($R^0$ or H$)_2$; N($R^0$ or H)—C(=O)—$R^0$; N($R^0$ or H)—C(=O)—N($R^0$ or H$)_2$; SH; SW; S(=O)$_2R^0$; S(=O)$_2$O($R^0$ or H); S(=O)$_2$—N($R^0$ or H$)_2$;

$R^7$, $R^8$, $R^9$, $R^{19}$ mutually independently stand for H; or $C_{1-4}$ alkyl, saturated or unsaturated, branched or unbranched, unsubstituted or mono- or polysubstituted;

$R^{11}$ and $R^{13}$ each independently stand for H; $C_{1-10}$ alkyl, saturated or unsaturated, branched or unbranched, unsubstituted or mono- or polysubstituted;

or $R^{11}$ and $R^{13}$ together with the carbon atoms binding them as ring members form a $C_{3-7}$ cycloalkyl or heterocyclyl, each saturated or unsaturated, unsubstituted or mono- or polysubstituted;

$R^{15}$ stands for $C_{3-10}$ alkyl, saturated or unsaturated, branched or unbranched, unsubstituted or mono- or polysubstituted; $C_{3-7}$ cycloalkyl, saturated or unsaturated, unsubstituted or mono- or polysubstituted; aryl or heteroaryl, unsubstituted or mono- or polysubstituted; $C_{1-8}$ alkyl-bridged $C_{3-7}$ cycloalkyl, saturated or unsaturated, unsubstituted or mono- or polysubstituted, wherein the alkyl chain can in each case be branched or unbranched, saturated or unsaturated, unsubstituted, mono- or polysubstituted; $C_{1-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted.

Compounds having the general formula (1) or (2) are particularly preferred wherein $R^1$ is selected from $C_{1-10}$ alkyl, preferably $C_{1-6}$ alkyl, $C_{3-7}$ cycloalkyl, preferably $C_{3-6}$ cycloalkyl, each branched or unbranched, saturated, unsubstituted; phenyl, unsubstituted or mono- or disubstituted with substituents mutually independently selected from the group consisting of F, Cl, $CH_3$, $OCH_3$ and $CF_3$; thienyl, unsubstituted or mono- or disubstituted with F, Cl, $CH_3$, $OCH_3$ or $CF_3$; pyridyl, unsubstituted or mono- or disubstituted with F, Cl, $CH_3$, $OCH_3$ or $CF_3$; $C_{1-3}$ alkyl-bridged phenyl, unsubstituted, wherein the alkyl chain is unbranched, saturated and unsubstituted;

$R^2$ is selected from H or $CH_3$, but preferably denotes H;

$R^3$, $R^4$, $R^5$ and $R^6$ each mutually independently denote H; F; Cl; $CH_3$; $OCH_3$ or $CF_3$;

$R^7$, $R^8$, $R^9$ and $R^{19}$ each mutually independently denote H or $CH_3$;

$R^{11}$, $R^{12}$, $R^{13}$ and $R^{14}$ each mutually independently denote H or $CH_3$;

$R^{15}$ stands for $C_{1-10}$ alkyl, saturated or unsaturated, branched or unbranched; phenyl, unsubstituted or mono- or disubstituted with substituents mutually independently selected from the group consisting of F, Cl, $CH_3$, $OCH_3$ and $CF_3$; $C_{1-4}$ alkyl-bridged phenyl, unsubstituted or mono- or disubstituted with substituents mutually independently selected from the group consisting of F, Cl, $CH_3$, $OCH_3$, $CF_3$, —O—$CH_2$—O—; $C_{1-4}$ alkyl-bridged naphthyl, thienyl, furanyl, indolyl or pyridyl, each unsubstituted; indazolyl, unsubstituted or monosubstituted with $CH_3$.

Compounds having the general formula (1) or (2) are most particularly preferred wherein $R^1$ is selected from methyl, prop-2-yl, 2-methyl-prop-2-yl and cyclohexyl; phenyl, unsubstituted; thienyl, unsubstituted; pyridyl, unsubstituted;

$R^2$ denotes H;

$R^3$ and $R^5$ each denote H;

$R^4$ and $R^6$ each mutually independently denote H; F; $CF_3$; $CH_3$; or $OCH_3$;

$R^7$, $R^8$, $R^9$ and $R^{19}$ each mutually independently denote H or $CH_3$;

$R^{11}$, $R^{12}$, $R^{13}$ and $R^{14}$ stand for H;

$R^{15}$ stands for $C_{1-4}$ alkyl, saturated and unbranched; phenyl, unsubstituted or mono- or disubstituted with substituents mutually independently selected from the group consisting of F, Cl, and $OCH_3$; benzyl, unsubstituted or mono- or disubstituted with substituents mutually independently selected from the group consisting of F; Cl; $CH_3$; $OCH_3$; $CF_3$; —O—$CH_2$—O—; $C_{2-4}$ alkyl-bridged phenyl, unsubstituted; $CH_2$-bridged naphthyl, thienyl, furanyl or pyridyl, each unsubstituted; $C_2H_4$-bridged indolyl, unsubstituted; indazolyl, monosubstituted with $CH_3$.

Particularly preferred are compounds from the group comprising:

1  4-Oxo-4-(1-phenyl-3,4-dihydroisoquinolin-2(1H)-yl)-N-(3-(trifluoromethyl)benzyl)butyric acid amide;

2  4-(1-Methyl-3,4-dihydro-1H-isoquinolin-2-yl)-4-oxo-N-[[3-(trifluoromethyl)phenyl]methyl]butyric acid amide;

3  4-Oxo-4-(1-thien-2-yl-3,4-dihydroisoquinolin-2(1H)-yl)-N-(3-(trifluoromethyl)benzyl)butyric acid amide;

4  4-Oxo-4-[1-(4-pyridyl)-3,4-dihydro-1H-isoquinolin-2-yl]-N-[[3-(trifluoromethyl)phenyl]methyl]butyric acid amide;

5  4-(7-Fluoro-1-phenyl-3,4-dihydroisoquinolin-2(1H)-yl)-4-oxo-N-(3-(trifluoromethyl)benzyl)butyric acid amide;

6  4-(5-Fluoro-1-phenyl-3,4-dihydro-1H-isoquinolin-2-yl)-4-oxo-N-[[3-(trifluoromethyl)phenyl]methyl]butyric acid amide;

7  4-Oxo-4-(1-phenyl-3,4-dihydro-1H-isoquinolin-2-yl)-N-[[2-(trifluoromethyl)phenyl]methyl]butyric acid amide;

8  4-Oxo-4-(1-phenyl-3,4-dihydro-1H-isoquinolin-2-yl)-N-[[4-(trifluoromethyl)phenyl]methyl]butyric acid amide;

9  4-(4-Methyl-1-phenyl-3,4-dihydro-1H-isoquinolin-2-yl)-4-oxo-N-[[3-(trifluoromethyl)phenyl]methyl]butyric acid amide;

10  4-(4,4-Dimethyl-1-phenyl-1,3-dihydroisoquinolin-2-yl)-4-oxo-N-[[3-(trifluoromethyl)phenyl]methyl]butyric acid amide;

11  4-(7-Methoxy-1-phenyl-3,4-dihydro-1H-isoquinolin-2-yl)-4-oxo-N-[[3-(trifluoromethyl)phenyl]methyl]butyric acid amide;

12  4-(5-Methoxy-1-phenyl-3,4-dihydro-1H-isoquinolin-2-yl)-4-oxo-N-[[3-(trifluoromethyl)phenyl]methyl]butyric acid amide;

13  4-(3-Methyl-1-phenyl-3,4-dihydro-1H-isoquinolin-2-yl)-4-oxo-N-[[3-(trifluoromethyl)phenyl]methyl]butyric acid amide;

14  N-(2-Chlorophenyl)-4-oxo-4-(1-phenyl-3,4-dihydro-1H-isoquinolin-2-yl)butyric acid amide;

15  N-(2,1,3-Benzothiadiazol-4-yl)-4-oxo-4-(1-phenyl-3,4-dihydro-1H-isoquinolin-2-yl)butyric acid amide;

16  N-(1-Methyl-6-indazolyl)-4-oxo-4-(1-phenyl-3,4-dihydro-1H-isoquinolin-2-yl)butyric acid amide;

17  N-(2-Furylmethyl)-4-oxo-4-(1-phenyl-3,4-dihydro-1H-isoquinolin-2-yl)butyric acid amide;

18  N-Benzyl-4-oxo-4-(1-phenyl-3,4-dihydro-1H-isoquinolin-2-yl)butyric acid amide;

19  4-Oxo-4-(1-phenyl-3,4-dihydro-1H-isoquinolin-2-yl)-N-(2-pyridylmethyl)butyric acid amide;

20  N-[(4-Methoxyphenyl)methyl]-4-oxo-4-(1-phenyl-3,4-dihydro-1H-isoquinolin-2-yl)butyric acid amide;

21  4-Oxo-N-phenethyl-4-(1-phenyl-3,4-dihydro-1H-isoquinolin-2-yl)butyric acid amide;

22  4-Oxo-4-(1-phenyl-3,4-dihydro-1H-isoquinolin-2-yl)-N-(4-pyridylmethyl)butyric acid amide;

23  4-Oxo-4-(1-phenyl-3,4-dihydro-1H-isoquinolin-2-yl)-N-(3-phenylpropyl)butyric acid amide;

24  N-[2-(1H-Indol-3-yl)ethyl]-4-oxo-4-(1-phenyl-3,4-dihydro-1H-isoquinolin-2-yl)butyric acid amide;

25  4-(5,7-Dimethyl-1-phenyl-3,4-dihydro-1H-isoquinolin-2-yl)-N-(4-methoxyphenyl)-4-oxobutyric acid amide;

26  N-(2-Chlorophenyl)-4-(5,7-dimethyl-1-phenyl-3,4-dihydro-1H-isoquinolin-2-yl)-4-oxobutyric acid amide;

27  4-(5,7-Dimethyl-1-phenyl-3,4-dihydro-1H-isoquinolin-2-yl)-N-(1-methyl-6-indazolyl)-4-oxobutyric acid amide;

28  4-(5,7-Dimethyl-1-phenyl-3,4-dihydro-1H-isoquinolin-2-yl)-N-(2-furylmethyl)-4-oxobutyric acid amide;

29  N-Benzyl-4-(5,7-dimethyl-1-phenyl-3,4-dihydro-1H-isoquinolin-2-yl)-4-oxobutyric acid amide;

30  4-(5,7-Dimethyl-1-phenyl-3,4-dihydro-1H-isoquinolin-2-yl)-4-oxo-N-(2-pyridylmethyl)butyric acid amide;

31  4-(5,7-Dimethyl-1-phenyl-3,4-dihydro-1H-isoquinolin-2-yl)-N-[(4-methoxyphenyl)methyl]-4-oxobutyric acid amide;

32  4-(5,7-Dimethyl-1-phenyl-3,4-dihydro-1H-isoquinolin-2-yl)-4-oxo-N-phenethylbutyric acid amide;

33  4-(5,7-Dimethyl-1-phenyl-3,4-dihydro-1H-isoquinolin-2-yl)-4-oxo-N-(3-phenylpropyl)butyric acid amide;

34  N-(4-Methoxyphenyl)-4-(5-methyl-1-phenyl-3,4-dihydro-1H-isoquinolin-2-yl)-4-oxobutyric acid amide;

35  N-(2-Chlorophenyl)-4-(5-methyl-1-phenyl-3,4-dihydro-1H-isoquinolin-2-yl)-4-oxobutyric acid amide;

36  N-(1-Methyl-6-indazolyl)-4-(5-methyl-1-phenyl-3,4-dihydro-1H-isoquinolin-2-yl)-4-oxobutyric acid amide;

37  N-(2-Furylmethyl)-4-(5-methyl-1-phenyl-3,4-dihydro-1H-isoquinolin-2-yl)-4-oxobutyric acid amide;

38  N-Benzyl-4-(5-methyl-1-phenyl-3,4-dihydro-1H-isoquinolin-2-yl)-4-oxobutyric acid amide;
39  4-(5-Methyl-1-phenyl-3,4-dihydro-1H-isoquinolin-2-yl)-4-oxo-N-(2-pyridylmethyl)butyric acid amide;
40  N-[(4-Methoxyphenyl)methyl]-4-(5-methyl-1-phenyl-3,4-dihydro-1H-isoquinolin-2-yl)-4-oxobutyric acid amide;
41  4-(5-Methyl-1-phenyl-3,4-dihydro-1H-isoquinolin-2-yl)-4-oxo-N-phenethylbutyric acid amide;
42  4-(5-Methyl-1-phenyl-3,4-dihydro-1H-isoquinolin-2-yl)-4-oxo-N-(3-phenylpropyl)butyric acid amide;
43  N-(4-Methoxyphenyl)-4-(7-methyl-1-phenyl-3,4-dihydro-1H-isoquinolin-2-yl)-4-oxobutyric acid amide;
44  N-(2-Chlorophenyl)-4-(7-methyl-1-phenyl-3,4-dihydro-1H-isoquinolin-2-yl)-4-oxobutyric acid amide;
45  N-(1-Methyl-6-indazolyl)-4-(7-methyl-1-phenyl-3,4-dihydro-1H-isoquinolin-2-yl)-4-oxobutyric acid amide;
46  N-(2-Furylmethyl)-4-(7-methyl-1-phenyl-3,4-dihydro-1H-isoquinolin-2-yl)-4-oxobutyric acid amide;
47  N-Benzyl-4-(7-methyl-1-phenyl-3,4-dihydro-1H-isoquinolin-2-yl)-4-oxobutyric acid amide;
48  4-(7-Methyl-1-phenyl-3,4-dihydro-1H-isoquinolin-2-yl)-4-oxo-N-(2-pyridylmethyl)butyric acid amide;
49  N-[(4-Methoxyphenyl)methyl]-4-(7-methyl-1-phenyl-3,4-dihydro-1H-isoquinolin-2-yl)-4-oxobutyric acid amide;
50  4-(7-Methyl-1-phenyl-3,4-dihydro-1H-isoquinolin-2-yl)-4-oxo-N-phenethylbutyric acid amide;
51  4-(7-Methyl-1-phenyl-3,4-dihydro-1H-isoquinolin-2-yl)-4-oxo-N-(4-pyridylmethyl)butyric acid amide;
52  4-Oxo-4-(1-phenyl-3,4-dihydro-1H-isoquinolin-2-yl)-N-(2-thienylmethyl)butyric acid amide;
53  N-[(2-Chlorophenyl)methyl]-4-oxo-4-(1-phenyl-3,4-dihydro-1H-isoquinolin-2-yl)butyric acid amide;
54  N-[(2,4-Dichlorophenyl)methyl]-4-oxo-4-(1-phenyl-3,4-dihydro-1H-isoquinolin-2-yl)butyric acid amide;
55  N-[(3,4-Dichlorophenyl)methyl]-4-oxo-4-(1-phenyl-3,4-dihydro-1H-isoquinolin-2-yl)butyric acid amide;
56  4-Oxo-4-(1-phenyl-3,4-dihydro-1H-isoquinolin-2-yl)-N-(p-tolylmethyl)butyric acid amide;
57  N-(1,3-Benzodioxol-5-ylmethyl)-4-oxo-4-(1-phenyl-3,4-dihydro-1H-isoquinolin-2-yl)butyric acid amide;
58  N-[(3-Fluorophenyl)methyl]-4-oxo-4-(1-phenyl-3,4-dihydro-1H-isoquinolin-2-yl)butyric acid amide;
59  N-[(2-Fluorophenyl)methyl]-4-oxo-4-(1-phenyl-3,4-dihydro-1H-isoquinolin-2-yl)butyric acid amide;
60  N-[(4-Fluorophenyl)methyl]-4-oxo-4-(1-phenyl-3,4-dihydro-1H-isoquinolin-2-yl)butyric acid amide;
61  N-[(2,5-Difluorophenyl)methyl]-4-oxo-4-(1-phenyl-3,4-dihydro-1H-isoquinolin-2-yl)butyric acid amide;
62  N-(1-Naphthylmethyl)-4-oxo-4-(1-phenyl-3,4-dihydro-1H-isoquinolin-2-yl)butyric acid amide;
63  4-(7-Methyl-1-phenyl-3,4-dihydro-1H-isoquinolin-2-yl)-4-oxo-N-propylbutyric acid amide;
64  4-(5-Methyl-1-phenyl-3,4-dihydro-1H-isoquinolin-2-yl)-4-oxo-N-propylbutyric acid amide;
65  4-(5,7-Dimethyl-1-phenyl-3,4-dihydro-1H-isoquinolin-2-yl)-4-oxo-N-propylbutyric acid amide;
66  4-Oxo-4-(1-phenyl-3,4-dihydro-1H-isoquinolin-2-yl)-N-propylbutyric acid amide;
67  4-Oxo-4-(1-(2-tolyl)-3,4-dihydro-1H-isoquinolin-2-yl)-N-[[3-(trifluoromethyl)-phenyl]methyl]butyric acid amide;
68  4-Oxo-4-(1-(2-tolyl)-3,4-dihydro-1H-isoquinolin-2-yl)-N-[[4-(trifluoromethyl)-phenyl]methyl]butyric acid amide;
69  4-Oxo-4-(1-(2-tolyl)-3,4-dihydro-1H-isoquinolin-2-yl)-N-[[2-(trifluoromethyl)-phenyl]methyl]butyric acid amide;
70  4-Oxo-4-(1-(2-tolyl)-6-methyl-3,4-dihydro-1H-isoquinolin-2-yl)-N-[[3-(trifluoromethyl)-phenyl]methyl]butyric acid amide;
71  4-(1-(2-Methyl-prop-2-yl)-3,4-dihydro-1H-isoquinolin-2-yl)-4-oxo-N-[[3-(trifluoromethyl)phenyl]methyl]butyric acid amide;
72  4-(1-Cyclohexyl-3,4-dihydro-1H-isoquinolin-2-yl)-4-oxo-N-[[3-(trifluoromethyl)-phenyl]methyl]butyric acid amide;
73  4-Oxo-4-(1-(2-fluorophenyl)-3,4-dihydro-1H-isoquinolin-2-yl)-N-[[3-(trifluoromethyl)phenyl]methyl]butyric acid amide;

or the physiologically compatible salts thereof.

The substituted tetrahydroisoquinolinyl-4-oxobutyric acid amides according to the invention and the corresponding acids, bases, salts and solvates are suitable as pharmaceutical active ingredients in medicinal products.

The invention therefore also provides a medicinal product containing at least one substituted tetrahydroisoquinolinyl-4-oxobutyric acid amide according to the invention having the general formula (1), wherein the radicals $R^1$ to $R^{15}$ have the meaning given above, and optionally one or more pharmaceutically compatible auxiliary substances.

The medicinal products according to the invention optionally contain, in addition to at least one compound according to the invention, suitable additives and/or auxiliary substances, including carrier materials, fillers, solvents, diluents, dyes and/or binders, and can be administered as liquid dosage forms in the form of injection solutions, drops or juices, as semi-solid dosage forms in the form of granules, tablets, pellets, patches, capsules, plasters/spray plasters or aerosols. The choice of auxiliary substances, etc., and the amount thereof to use depend on whether the medicinal product is to be administered by oral, peroral, parenteral, intravenous, intraperitoneal, intradermal, intramuscular, intranasal, buccal, rectal or local means, for example on the skin, mucous membranes or in the eyes. Preparations in the form of tablets, pastilles, capsules, granules, drops, juices and syrups are suitable for oral administration; solutions, suspensions, easily reconstitutable dry preparations and sprays are suitable for parenteral, topical and inhalative administration. Compounds according to the invention in a depot formulation, in dissolved form or in a plaster, optionally with addition of agents promoting skin penetration, are suitable preparations for percutaneous administration. Preparation forms suitable for oral or percutaneous administration can deliver the compounds according to the invention on a delayed release basis. The compounds according to the invention can also be used in parenteral long-term depot forms, such as implants or implanted pumps, for example. Other additional active ingredients known to the person skilled in the art can be added in principle to the medicinal products according to the invention.

These medicinal products according to the invention are suitable for influencing KCNQ2/3 channels and exert an agonistic or antagonistic, in particular an agonistic, action.

The medicinal products according to the invention are preferably suitable for the treatment of disorders or diseases which are at least partly mediated by KCNQ2/3 channels.

The medicinal products according to the invention are preferably suitable for the treatment of one or more diseases chosen from the group consisting of pain, preferably pain chosen from the group consisting of acute pain, chronic pain, neuropathic pain, muscular pain and inflammatory pain, epilepsy, urinary incontinence, anxiety states, dependency, mania, bipolar disorders, migraine, cognitive diseases, dystonia-associated dyskinesias and/or urinary incontinence.

The medicinal products according to the invention are particularly preferably suitable for the treatment of pain, most particularly preferably chronic pain, neuropathic pain, inflammatory pain and muscular pain.

The medicinal products according to the invention are further particularly preferably suitable for the treatment of epilepsy.

The invention also provides the use of at least one substituted tetrahydroisoquinolinyl-4-oxobutyric acid amide according to the invention and optionally one or more pharmaceutically compatible auxiliary substances for the preparation of a medicinal product for the treatment of disorders or diseases which are at least partly mediated by KCNQ2/3 channels.

Preference is given to the use of at least one substituted tetrahydroisoquinolinyl-4-oxobutyric acid amide according to the invention and optionally one or more pharmaceutically compatible auxiliary substances for the preparation of a medicinal product for the treatment of pain, preferably pain chosen from the group consisting of acute pain, chronic pain, neuropathic pain, muscular pain and inflammatory pain; epilepsy, urinary incontinence, anxiety states, dependency, mania, bipolar disorders, migraine, cognitive diseases, dystonia-associated dyskinesias and/or urinary incontinence.

Particularly preferred is the use of at least one substituted tetrahydroisoquinolinyl-4-oxobutyric acid amide according to the invention and optionally one or more pharmaceutically compatible auxiliary substances for the preparation of a medicinal product for the treatment of pain, most particularly preferably chronic pain, neuropathic pain, inflammatory pain and muscular pain.

Also particularly preferred is the use of at least one substituted tetrahydroisoquinolinyl-4-oxobutyric acid amide according to the invention and optionally one or more pharmaceutically compatible auxiliary substances for the preparation of a medicinal product for the treatment of epilepsy.

The invention also provides at least one substituted tetrahydroisoquinolinyl-4-oxobutyric acid amide according to the invention and optionally one or more pharmaceutically compatible auxiliary substances for the treatment of disorders or diseases which are at least partly mediated by KCNQ2/3 channels.

The invention also provides at least one substituted tetrahydroisoquinolinyl-4-oxobutyric acid amide according to the invention and optionally one or more pharmaceutically compatible auxiliary substances for the treatment of pain, preferably pain chosen from the group consisting of acute pain, chronic pain, neuropathic pain, muscular pain and inflammatory pain; epilepsy, urinary incontinence, anxiety states, dependency, mania, bipolar disorders, migraine, cognitive diseases, dystonia-associated dyskinesias and/or urinary incontinence.

Particularly preferred is at least one substituted tetrahydroisoquinolinyl-4-oxobutyric acid amide according to the invention and optionally one or more pharmaceutically compatible auxiliary substances for the treatment of pain, most particularly preferably chronic pain, neuropathic pain, inflammatory pain and muscular pain.

Particularly preferred is also at least one substituted tetrahydroisoquinolinyl-4-oxobutyric acid amide according to the invention and optionally one or more pharmaceutically compatible auxiliary substances for the treatment of epilepsy.

The invention also provides the use of at least one substituted tetrahydroisoquinolinyl-4-oxobutyric acid amide according to the invention and optionally one or more pharmaceutically compatible auxiliary substances for the treatment of disorders or diseases which are at least partly mediated by KCNQ2/3 channels.

Preference is given to the use of at least one substituted tetrahydroisoquinolinyl-4-oxobutyric acid amide according to the invention and optionally one or more pharmaceutically compatible auxiliary substances for the treatment of pain, preferably pain chosen from the group consisting of acute pain, chronic pain, neuropathic pain, muscular pain and inflammatory pain; epilepsy, urinary incontinence, anxiety states, dependency, mania, bipolar disorders, migraine, cognitive diseases, dystonia-associated dyskinesias and/or urinary incontinence.

The effectiveness against pain can be demonstrated for example in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363). The effectiveness against epilepsy can be demonstrated for example in the DBA/2 mouse model (De Sarro et al., Naunyn-Schmiedeberg's Arch. Pharmacol. 2001, 363, 330-336).

The substituted tetrahydroisoquinolinyl-4-oxobutyric acid amides according to the invention preferably have an $EC_{50}$ value of at most 11 µM or at most 5 µM, more preferably at most 3 µM or at most 2 µM, even more preferably at most 1.5 µM or at most 1 µM, most preferably at most 0.8 µM or at most 0.6 µM and in particular at most 0.4 µM or at most 0.2 µM. Methods for determining the $EC_{50}$ value are known to the person skilled in the art. The $EC_{50}$ value is preferably determined by fluorimetry, particularly preferably by the method described in "Pharmacological experiments".

The invention also provides methods for preparing the substituted tetrahydroisoquinolinyl-4-oxobutyric acid amides according to the invention.

The chemicals and reaction components used in the reactions described below are available commercially or can be produced by conventional methods known to the person skilled in the art.

General Preparation Methods
Scheme 1:
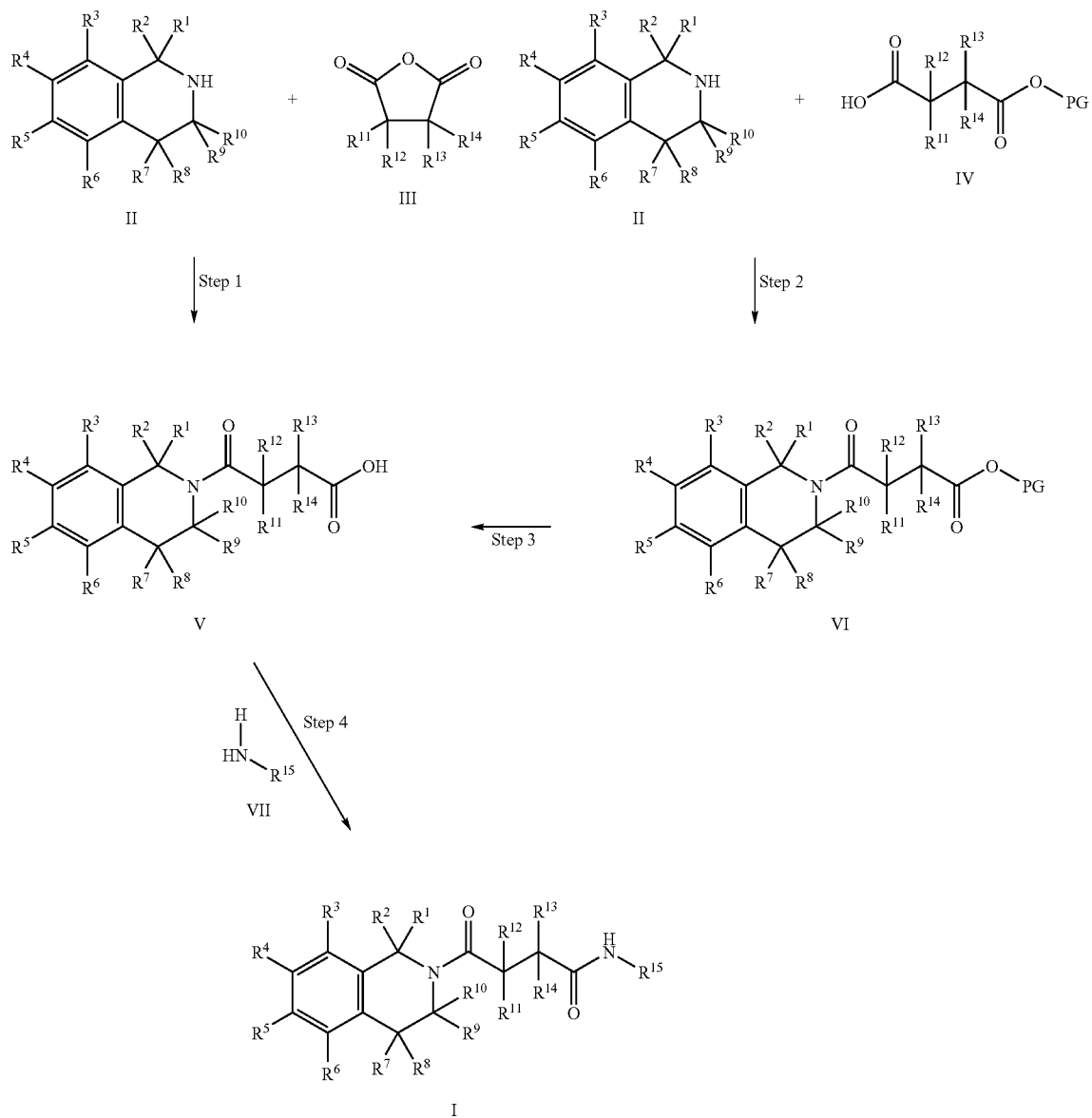
Scheme 2:
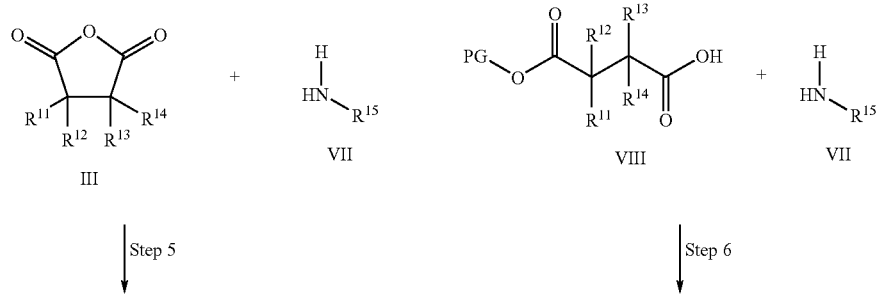

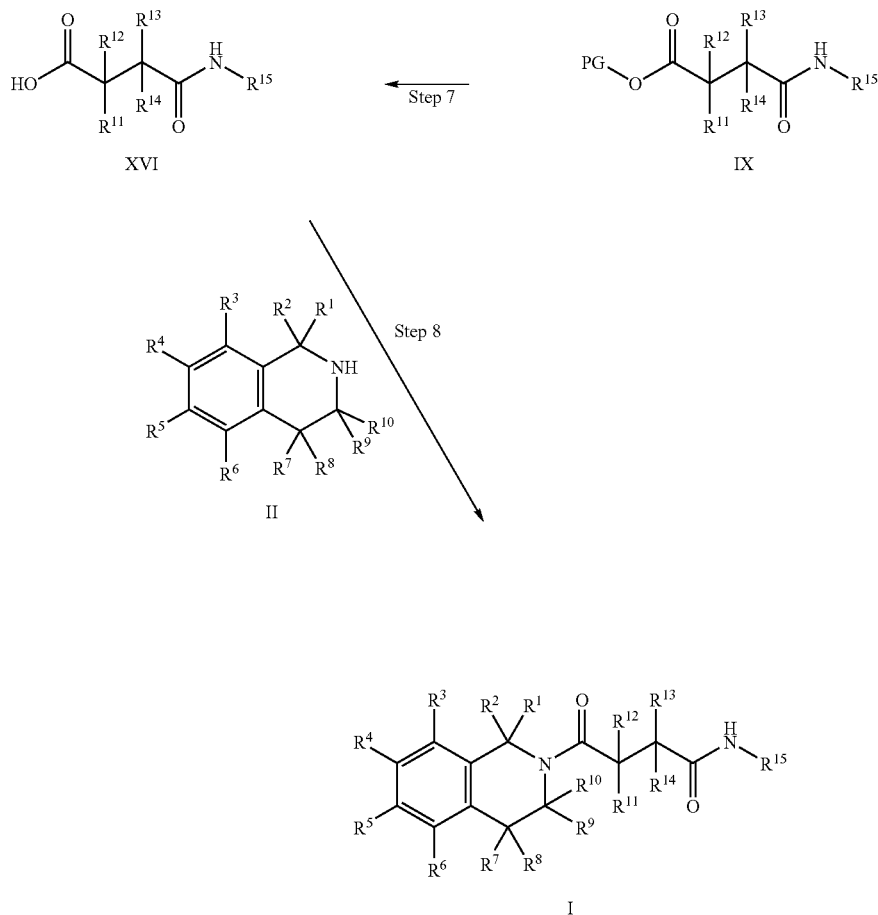

In step 1, amines having the general formula II are reacted with succinic anhydrides having the general formula III, in a reaction medium, preferably selected from the group consisting of acetone, acetonitrile, chloroform, dioxane, dichloromethane, ethanol, ethyl acetate, nitrobenzene, methanol and tetrahydrofuran, optionally in the presence of an inorganic base, preferably potassium carbonate, or an organic base, preferably selected from the group consisting of triethylamine, pyridine, dimethylaminopyridine and diisopropylethylamine, preferably at temperatures of −20° C. to 160° C., to form carboxylic acids having the general formula V.

In step 2, carboxylic acids having the general formula IV, wherein PG stands for a $C_{1-6}$ alkyl group, preferably methyl, ethyl, isopropyl or tert-butyl, are reacted with amines having the general formula II by the method described in step 4 to form compounds having the general formula VI.

Alternatively in step 2, compounds having the general formula IV, wherein PG stands for a $C_{1-6}$ alkyl group, preferably methyl, ethyl, isopropyl or tert-butyl, are first activated at the acid function, for example by conversion into the corresponding acid halide, preferably acid chloride, or into reactive esters, preferably pentafluorophenolic esters, and then reacted with amines having the general formula II in a reaction medium, preferably selected from the group consisting of diethyl ether, tetrahydrofuran, acetonitrile, methanol, ethanol, dimethyl formamide and dichloromethane, with or without the addition of at least one organic or inorganic base, for example triethylamine, dimethylaminopyridine, pyridine or diisopropylamine, optionally in the presence of at least one organic base, preferably selected from the group consisting of triethylamine, dimethylaminopyridine, pyridine and diisopropylamine, or an organic base, at temperatures of preferably −20° C. to 100° C., to form compounds having the general formula VI.

In step 3, carboxylic acid esters having the general formula VI, wherein PG stands for a $C_{1-6}$ alkyl group, preferably methyl, ethyl, isopropyl or tert-butyl, are cleaved, optionally in a reaction medium, preferably selected from the group consisting of acetone, acetonitrile, chloroform, dioxane, dichloromethane, ethanol, methanol, tetrahydrofuran and water or in a mixture of these reaction media, optionally in the presence of an inorganic base, preferably LiOH or NaOH, or optionally in the presence of an acid, preferably formic acid, hydrochloric acid or trifluoroacetic acid, optionally in the presence of triethylsilane, triisopropylsilane or ethanediol, preferably at temperatures of −20° C. to 80° C., to form carboxylic acids having the general formula V.

In step 4, carboxylic acids having the general formula V are reacted with amines having the general formula VII, in a reaction medium, preferably selected from the group consisting of diethyl ether, tetrahydrofuran, acetonitrile, methanol, ethanol, dimethyl formamide and dichloromethane, optionally in the presence of at least one coupling reagent, preferably selected from the group consisting of 1-benzotriazolyloxy-tris-(dimethylamino)phosphonium hexafluorophosphate (BOP), dicyclohexylcarbodiimide (DCC), diisopropylcarbodiimide (DIC), N'-(3-dimethylaminopropyl)-N-ethylcarbodiimide (EDCI), N-[(dimethylamino)-1H-1,2,3-triazolo[4,5-b]pyridino-1-ylmethylene]-N-methylmethanaminium hexafluorophosphate N-oxide (HATU), 0-(benzotriazol-1-yl)-N,N,N',N'-tetramethyluronium hexafluorophosphate (HBTU) and 1-hydroxy-7-azabenzotriazole (HOAt), optionally in the presence of at least one inorganic base, preferably selected from the group consisting of potassium carbonate and caesium carbonate, or an organic base, preferably selected from the group consisting of triethylamine, pyridine, dimethylaminopyridine and diisopropylethylamine, preferably at temperatures of −70° C. to 150° C., to form compounds having the general formula I.

In step 5, amines having the general formula VII are reacted with succinic anhydrides having the general formula III, by the method described in step 1, to form carboxylic acids having the general formula XVI.

In step 6, amines having the general formula VII are reacted with carboxylic acids having the general formula VIII, by the method described in step 2, to form compounds having the general formula IX.

In step 7, carboxylic acid esters having the general formula IX, wherein PG stands for a $C_{1-6}$ alkyl group, preferably methyl, ethyl, isopropyl or tert-butyl, are cleaved by the method described in step 3 to form carboxylic acids having the general formula XVI.

In step 8, amines having the general formula II are reacted with carboxylic acids having the general formula XVI, by the method described in step 4, to form compounds having the general formula I.

Scheme 3 (Pictet-Spengler synthesis):

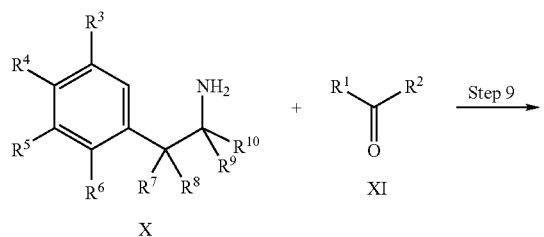

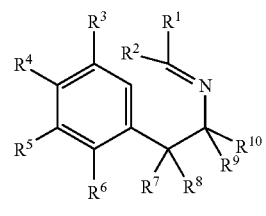

XII

Step 10

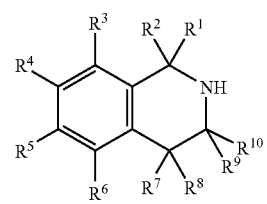

II

In step 9, amines having the general formula X are reacted with ketones or aldehydes ($R^2$=H) having the general formula XI, in a reaction medium, preferably selected from the group consisting of acetonitrile, chloroform, dichloromethane, diethyl ether, ethanol, methanol, tetrahydrofuran, toluene and xylene, optionally in the presence of an inorganic base, preferably potassium carbonate, or an organic base, preferably selected from the group consisting of triethylamine, pyridine, dimethylaminopyridine and diisopropylethylamine, preferably at temperatures of 0° C. to 160° C., to form imines having the general formula XII.

In step 10, imines having the general formula XII are cyclised, optionally in a reaction medium, preferably selected from the group consisting of benzene, ethanol, methanol, toluene, water and xylene, with the addition of an acid, preferably selected from the group consisting of hydrochloric acid, trifluoroacetic acid or trifluoromethanesulfonic acid, preferably at temperatures of 0° C. to 160° C., to form compounds having the general formula II.

Scheme 4 (Bischler-Napieralski synthesis):

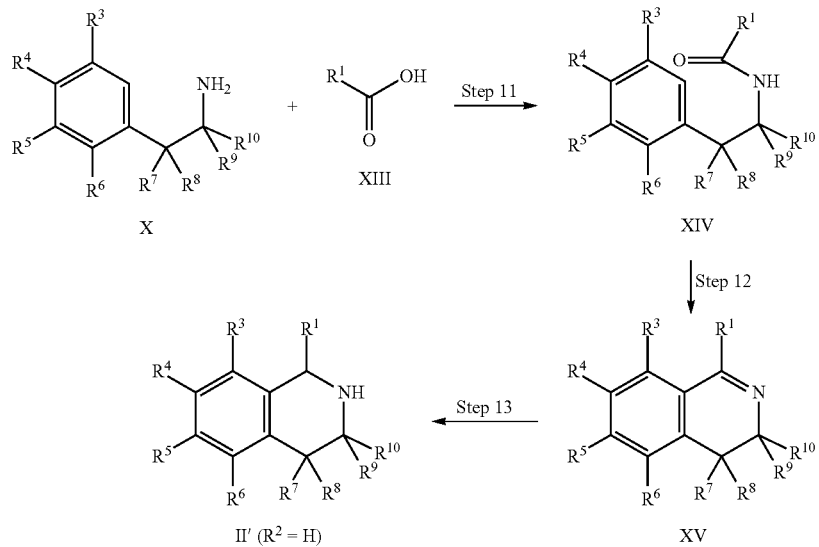

In step 11, amines having the general formula X are reacted with carboxylic acids having the general formula XIII, by the method described in step 4, to form amides having the general formula XIV.

In step 12, amides having the general formula XIV are cyclised in a reaction medium, preferably selected from the group consisting of benzene, chloroform, toluene or xylene, in the presence of a suitable cyclisation reagent, preferably phosphoryl trichloride or phosphorus pentachloride, optionally with the addition of phosphorus pentoxide, preferably at temperatures of 20° C. to 150° C., to form compounds having the general formula XV.

In step 13, compounds having the general formula XIV are reduced in a reaction medium, preferably selected from the group consisting of diethyl ether, ethanol, acetic acid, methanol and tetrahydrofuran, in the presence of a suitable reducing agent, preferably selected from the group consisting of sodium boron hydride, sodium cyanoboron hydride, lithium aluminium hydride or hydrogen, optionally with the addition of a catalyst, preferably selected from the group consisting of palladium, platinum, platinum oxide or Raney nickel, optionally with the addition of an organic base selected from the group consisting of ammonia, triethylamine and diisopropyl ethylamine, preferably at temperatures of −20° C. to 100° C., to form compounds having the general formula II' ($R^2$=H).

DESCRIPTION OF THE EXAMPLE SYNTHESES

Abbreviations

AcOH acetic acid
aq. aqueous
brine saturated aqueous NaCl solution
d days
DCM dichloromethane
DIPEA N,N-diisopropylethylamine
EDC N-(3-dimethylaminopropyl)-N'-ethyl carbodiimide hydrochloride
EE ethyl acetate
ether diethyl ether
sat. saturated
h hour(s)
HATU O-(7-azabenzotriazol-1-yl)-N,N,N',N'-tetramethyluronium hexafluorophosphate
HOAt 7-aza-1-hydroxy-1H-benzotriazole
HOBt 1-hydroxy-1H-benzotriazole
sol. solution
m/z mass-to-charge ratio
M molar
MeCN acetonitrile
MeOH methanol
max. maximum
min minutes
MS mass spectrometry
N/A not available
$NEt_3$ triethylamine
PS carbodiimide a polymer-bound carbodiimide having the following structure:

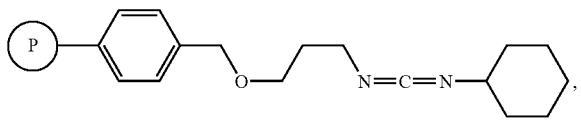

Loading: 0.9-1.4 mmol/g
Particle size: 75-150 μm
PPA polyphosphoric acid
RG retigabine
RT room temperature 23±7° C.
SC column chromatography on silica gel
THF tetrahydrofuran
vv ratio by volume All starting materials not explicitly described were either available commercially (suppliers can be found for example in the Symyx® Available Chemicals Database from MDL, San Ramon, US), or their synthesis is already accurately described in the specialist literature (experimental procedures can be found for example in the Reaxys® database from Elsevier, Amsterdam, NL), or can be prepared by methods known to the person skilled in the art.

Silica gel 60 (0.040-0.063 mm) was used as the stationary phase for column chromatography (SC).

The analytical characterisation of all intermediates and example compounds was performed by means of $^1$H-NMR spectroscopy. An analysis by mass spectrometry (MS, m/z stated for [M+H]$^+$) was also performed for all example compounds and selected intermediates.

Synthesis of Intermediates

Synthesis of intermediate VVV01:
4-Oxo-4-(3-(trifluoromethyl)benzylamino)butyric acid A solution of 15.0 g (85.6 mmol) of (3-(trifluoromethyl)phenyl)methylamine in ether (40 ml) was added dropwise to a suspension of 7.5 g (85.6 mmol) of succinic anhydride in ether (450 ml) within 30 min. The mixture was then stirred for 72 h at room temperature. The deposit obtained was filtered and dried. After column chromatography (EE/MeOH 1:1) of the residue, 10.4 g (37.8 mmol, 44%) of 4-oxo-4-(3-(trifluoromethyl)benzylamino)butyric acid were obtained.

Synthesis of intermediate VVV04: 4-(7-Fluoro-1-phenyl-3,4-dihydroisoquinolin-2(1H)-yl)-4-oxobutyric acid a) Synthesis of N-(4-fluorophenethyl)benzamide 1.5 g (10.8 mmol) of HOAt were added to a solution of 15.0 g (108.0 mmol) of 4-fluorophenethylamine and 13.2 g (108.0 mmol) of benzoic acid in DCM and the mixture was then cooled to 0° C. 22.8 g (119.0 mmol) of EDC were then added at this temperature and the mixture was then stirred for 16 h at RT. The reaction solution was then washed successively with a 1M aqueous hydrochloric acid (2×300 ml), a 2M aqueous NaOH solution (300 ml) and brine (200 ml). The organic phase was dried over Na$_2$SO$_4$, filtered and concentrated to small volume under vacuum. 20.5 g (84.2 mmol, 78%) of N-(4-fluorophenethyl)benzamide were obtained as the residue.

b) Synthesis of 7-fluoro-1-phenyl-3,4-dihydroisoquinoline

A mixture of 12.5 g (51.4 mmol) of N-(4-fluorophenethyl)benzamide and polyphosphoric acid (150 ml) was heated at 150° C. for 5 days. Then the hot solution was poured into water and the reaction was quenched by the addition of NaHCO$_3$. It was extracted with DCM (3×300 ml). The combined organic phases were washed with brine (300 ml), dried over Na$_2$SO$_4$, filtered and concentrated to small volume under vacuum. 3.2 g of the crude product 7-fluoro-1-phenyl-3,4-dihydroisoquinoline were obtained as the residue, which was reacted further with no additional purification.

c) Synthesis of 7-fluoro-1-phenyl-1,2,3,4-tetrahydroisoquinoline 0.65 g (17.1 mmol) of NaBH$_4$ were added in portions to a solution of 3.2 g (max. 14.2 mmol) of the crude product 7-fluoro-1-phenyl-3,4-dihydroisoquinoline in EtOH (80 ml) and the mixture was then stirred for 16 h at RT. Then the mixture was concentrated to small volume under vacuum and the residue was taken up with DCM (200 ml). It was washed with water and the aqueous phase was extracted with DCM (2×150 ml). The combined organic phases were washed with brine, dried over Na$_2$SO$_4$, filtered and concentrated to small volume under vacuum. 7-Fluoro-1-phenyl-1,2,3,4-tetrahydroisoquinoline was obtained as the crude product, which was reacted further with no additional purification.

d) Synthesis of 4-(7-fluoro-1-phenyl-3,4-dihydroisoquinolin-2(1H)-yl)-4-oxobutyric acid 5.0 g (49.7 mmol) of succinic anhydride and 4.0 ml (28.4 mmol) of NEt$_3$ were added in succession to a solution of the crude product 7-fluoro-1-phenyl-1,2,3,4-tetrahydroisoquinoline (max. 14.2 mmol) in MeCN (200 ml) and the mixture was then stirred for 16 h at RT. It was then concentrated to small volume under vacuum and the residue was taken up with a saturated aqueous NaHCO$_3$ solution (300 ml). It was extracted with DCM (2×200 ml). The combined organic phases were washed with a 1M aqueous hydrochloric acid (200 ml), dried over Na$_2$SO$_4$, filtered and concentrated to small volume under vacuum. Column chromatography (heptane/EE 1:1+1% AcOH) of the residue produced 1.72 g (5.3 mmol, 10% over 3 stages) of 4-(7-fluoro-1-phenyl-3,4-dihydroisoquinolin-2(1H)-yl)-4-oxobutyric acid.

Synthesis of intermediate VVV06: 4-(7-Methoxy-1-phenyl-3,4-dihydroisoquinolin-2(1H)-yl)-4-oxobutyric acid a) Synthesis of N-(4-methoxyphenethyl)benzamide The synthesis of 4.98 g (19.5 mmol, 98%) of N-(4-methoxyphenethyl)benzamide took place by the method described for intermediate VVV04 in a).

b) Synthesis of 7-methoxy-1-phenyl-3,4-dihydroisoquinoline

A mixture of 4.0 g (15.7 mmol) of N-(4-methoxyphenethyl)benzamide and 21.1 ml (227.0 mmol) of POCl$_3$ in MeCN (120 ml) was refluxed for 16 h. The mixture was then concentrated to small volume under vacuum, taken up with MeOH and concentrated to small volume under vacuum again. This step was repeated three times. 24.65 g of the crude product 7-methoxy-1-phenyl-3,4-dihydroisoquinoline were obtained as the residue, which was reacted further with no additional purification.

c) Synthesis of 7-methoxy-1-phenyl-1,2,3,4-tetrahydroisoquinoline 24.65 g (max. 15.7 mmol) of the crude product from b) were reacted by the method described for intermediate VVV04 in c) to form 7-methoxy-1-phenyl-1,2,3,4-tetrahydroisoquinoline. The 6.81 g of crude product that were obtained were used with no further purification.

d) Synthesis of 4-(7-methoxy-1-phenyl-3,4-dihydroisoquinolin-2(1H)-yl)-4-oxobutyric acid 6.81 g of the crude product from c) were reacted by the method described for intermediate VVV04 in d) to form 4-(7-methoxy-1-phenyl-3,4-dihydroisoquinolin-2(1H)-yl)-4-oxobutyric acid. 2.2 g (6.5 mmol, 41% over 3 stages) of 4-(7-methoxy-1-phenyl-3,4-dihydroisoquinolin-2(1H)-yl)-4-oxobutyric acid were obtained.

Synthesis of intermediate VVV09: 4-(7-Methyl-1-phenyl-3,4-dihydroisoquinolin-2(1H)-yl)-4-oxobutyric acid a) Synthesis of 7-methyl-1-phenyl-1,2,3,4-tetrahydroisoquinoline

A mixture of 12.0 g (89 mmol) of 2-p-tolylethylamine and 11.21 ml (111 mmol) of benzaldehyde in PPA (300 g) was heated at 100° C. for 5 days. After cooling to RT it was poured into a saturated aqueous $K_2CO_3$ solution (1200 ml). Following the addition of DCM (300 ml) it was stirred for 50 min at RT. Then the phases were separated and the aqueous phase was extracted with DCM (2×500 ml). The organic phases were combined, dried over $Na_2SO_4$, filtered and concentrated to small volume under vacuum. 16.3 g of 7-methyl-1-phenyl-1,2,3,4-tetrahydroisoquinoline were obtained as the crude product, which was reacted further with no additional purification.

b) Synthesis of 4-(7-methyl-1-phenyl-3,4-dihydroisoquinolin-2(1H)-yl)-4-oxobutyric acid 25.5 g (255 mmol) of succinic anhydride and 20.3 ml (146 mmol) of $NEt_3$ were added in succession to a solution of 16.3 g of the crude product 7-methyl-1-phenyl-1,2,3,4-tetrahydroisoquinoline from a) in MeCN (300 ml) and the mixture was stirred for 16 h at RT. It was then concentrated to small volume under vacuum. The residue was taken up with DCM (400 ml). It was then washed with a saturated aqueous $NaHCO_3$ solution. The aqueous phase was extracted with DCM (2×400 ml). The collected organic phases were washed with 1N aqueous hydrochloric acid (400 ml) and with brine, dried over $Na_2SO_4$, filtered and concentrated to small volume under vacuum. Column chromatography (gradient heptane/EE 1:1 heptane/EE/AcOH 2:2:1) of the residue and subsequent crystallisation of the residue from EE produced 6.79 g (21 mmol, 24% over 2 stages) of 4-(7-methyl-1-phenyl-3,4-dihydroisoquinolin-2(1H)-yl)-4-oxobutyric acid.

Synthesis of intermediate VVV12: 4-Methyl-1-phenyl-1,2,3,4-tetrahydroisoquinoline 4 Å molecular sieve (10 g) was added to a solution of 1.06 g (10.0 mmol) of benzaldehyde and 1.35 g (10.0 mmol) of 2-phenylpropylamine in toluene (45 ml) and the mixture was refluxed for 4 h. After cooling to RT the mixture was filtered through diatomaceous earth and the filtrate was concentrated to small volume under vacuum. The residue was dissolved in TFA (90 ml) and the solution was heated at 120° C. for 20 h. Then it was concentrated to small volume under vacuum and made alkaline with a 2N aqueous NaOH solution. It was then extracted with EE. The organic phase was dried over $Na_2SO_4$, filtered and concentrated to small volume under vacuum. Column chromatography (hexane/EE 7:3) of the residue produced 1.74 g (7.8 mmol, 78%) of 4-methyl-1-phenyl-1,2,3,4-tetrahydroisoquinoline.

Synthesis of intermediate VVV14: 4,4-Dimethyl-1-phenyl-1,2,3,4-tetrahydroisoquinoline a) Synthesis of N-(2-methyl-2-phenylpropyl)benzamide 4.0 ml (30 mmol) of $NEt_3$ and 4.22 g (30 mmol) of benzoylchloride were added in succession at 0° C. to a solution of 1.86 g (10.0 mmol) of 2-methyl-2-phenylpropylamine hydrochloride in DCM (30 ml) and the mixture was stirred for 1 h at RT. It was then diluted with DCM and washed with a 10% aqueous hydrochloric acid, a saturated aqueous $Na_2CO_3$ solution and brine. The organic phase was dried over $Na_2SO_4$, filtered and concentrated to small volume under vacuum. 2.48 g (9.8 mmol, 98%) of N-(2-methyl-2-phenylpropyl)benzamide were obtained as the residue, which was reacted further with no additional purification.

b) Synthesis of 4,4-dimethyl-1-phenyl-3,4-dihydroisoquinoline 1.42 g (10.0 mmol) of $P_2O_5$ and $POCl_3$ (4 ml) were added to a solution of 1.27 g (5.0 mmol) of N-(2-methyl-2-phenylpropyl)benzamide in xylene (20 ml) and the mixture was heated at 150° C. for 3 h. After cooling to RT the mixture was concentrated to small volume under vacuum. The residue was made alkaline with a 20% aqueous NaOH solution. It was then extracted with EE and the organic phase was dried over $Na_2SO_4$, filtered and concentrated to small volume under vacuum. 634 mg (2.7 mmol) of 4,4-dimethyl-1-phenyl-3,4-dihydroisoquinoline were obtained as the residue, which was reacted further with no additional purification.

c) Synthesis of 4,4-dimethyl-1-phenyl-1,2,3,4-tetrahydroisoquinoline

A solution of 471 mg (2.0 mmol) of 4,4-dimethyl-1-phenyl-3,4-dihydroisoquinoline in MeOH (6 ml) was cooled to 0° C. and 151 mg (4.0 mmol) of $NaBH_4$ were added in portions. After stirring for 3 h at RT a saturated aqueous $NH_4Cl$ solution was added. Then most of the methanol was removed under vacuum and the residue was extracted with EE. The organic phase was washed with brine, dried over $Na_2SO_4$, filtered and concentrated to small volume under vacuum. 19 mg (0.08 mmol, 4%) of 4,4-dimethyl-1-phenyl-1,2,3,4-tetrahydroisoquinoline were obtained as the residue, which was reacted further with no additional purification.

Synthesis of Further Intermediates

The synthesis of further intermediates took place by the methods already described. Table 1 shows which compound was prepared by which method. The starting materials and reagents used in each case are apparent to the person skilled in the art.

TABLE 1

| Intermediate | Chemical name | Preparation analogous to intermediate | Yield [%] |
|---|---|---|---|
| VVV02 | 4-Oxo-4-(2-(trifluoromethyl)benzylamino)butyric acid | VVV01 | 28 |
| VVV03 | 4-Oxo-4-(4-(trifluoromethyl)benzylamino)butyric acid | VVV01 | 30 |
| VVV05 | 4-(5-Fluoro-1-phenyl-3,4-dihydroisoquinolin-2(1H)-yl)-4-oxobutyric acid | VVV04 | 12 (4 stages) |
| VVV07 | 4-(5-Methoxy-1-phenyl-3,4-dihydroisoquinolin-2(1H)-yl)-4-oxobutyric acid | VVV06 | 51 (4 stages) |
| VVV08 | 4-(1-Phenyl-3,4-dihydroisoquinolin-2(1H)-yl)-4-oxobutyric acid | VVV04 d) | 58 |
| VVV10 | 4-(5-Methyl-1-phenyl-3,4-dihydroisoquinolin-2(1H)-yl)-4-oxobutyric acid | VVV09 | 25 (2 stages) |

TABLE 1-continued

| Inter-mediate | Chemical name | Preparation analogous to intermediate | Yield [%] |
|---|---|---|---|
| VVV11 | 4-(5,7-Dimethyl-1-phenyl-3,4-dihydroisoquinolin-2(1H)-yl)-4-oxobutyric acid | VVV09 | 30 (2 stages) |
| VVV13 | 3-Methyl-1-phenyl-1,2,3,4-tetrahydroisoquinoline | VVV12 | 39 |
| VVV15 | 4-(1-(2-Tolyl)-3,4-dihydroisoquinolin-2(1H)-yl)-4-oxobutyric acid | VVV09 | 75 (2 stages) |
| VVV16 | 4-(1-Cyclohexyl-3,4-dihydroisoquinolin-2(1H)-yl)-4-oxobutyric acid | VVV09 | 58 (2 stages) |
| VVV17 | 4-(1-(2-Methyl-prop-2-yl)-3,4-dihydroisoquinolin-2(1H)-yl)-4-oxobutyric acid | VVV09 | 98 (2 stages) |
| VVV18 | 4-(1-(2-Fluorophenyl)-3,4-dihydroisoquinolin-2(1H)-yl)-4-oxobutyric acid | VVV09 | 84 (2 stages) |

Synthesis of the Example Compounds

Synthesis of example compound 1: 4-Oxo-4-(1-phenyl-3,4-dihydroisoquinolin-2(1H)-yl)-N-(3-(trifluoromethyl)benzyl)butyric acid amide 1.98 g (~2.0 mmol) of PS carbodiimide resin were added to a solution of 209 mg (1.0 mmol) of 1-phenyl-1,2,3,4-tetrahydroisoquinoline and 275 mg (1.0 mmol) of 4-oxo-4-(3-(trifluoromethyl)benzylamino)butyric acid (intermediate VVV01) in a mixture of DCM and DMF (82 ml, 40:1 vv) and the mixture was shaken for 16 h at RT. Then the resin was filtered off and it was washed with DCM and MeOH. The filtrate was concentrated to small volume under vacuum. Column chromatography (DCM/EtOH 40:1) of the residue produced 287 mg (0.6 mmol, 62%) of 4-oxo-4-(1-phenyl-3,4-dihydroisoquinolin-2(1H)-yl)-N-(3-(trifluoromethyl)benzyl)butyric acid amide. MS: m/z 467.2 [M+H]$^+$.

Synthesis of example compound 3: 4-Oxo-4-(1-thien-2-yl-3,4-dihydroisoquinolin-2(1H)-yl)-N-(3-(trifluoromethyl)benzyl)butyric acid amide 236 mg (1.1 mmol) of 1-(thiophen-2-yl)-1,2,3,4-tetrahydroisoquinoline, 380 mg (1.0 mmol) of HATU and 263 µl (1.9 mmol) of NEt$_3$ were added in succession to a solution of 275 mg (1.0 mmol) of 4-oxo-4-(3-(trifluoromethyl)benzylamino) butyric acid (intermediate VVV01) in THF (8 ml) and the mixture was then stirred for 24 h at RT. Then it was diluted with EE (30 ml) and washed twice with a 4M aqueous NH$_4$Cl solution and with a 1M aqueous NaHCO$_3$ solution. The organic phase was dried over MgSO$_4$, filtered and concentrated to small volume under vacuum. Column chromatography (EE) of the residue produced 410 mg (0.87 mmol, 87%) of 4-oxo-4-(1-thien-2-yl-3,4-dihydroisoquinolin-2(1H)-yl)-N-(3-(trifluoromethyl)benzyl)butyric acid amide. MS: m/z 473.1 [M+H]$^+$.

Synthesis of example compound 5: 4-(7-Fluoro-1-phenyl-3,4-dihydroisoquinolin-2(1H)-yl)-4-oxo-N-(3-(trifluoromethyl)benzyl)butyric acid amide A solution of 200 mg (0.61 mmol) of 4-(7-fluoro-1-phenyl-3,4-dihydroisoquinolin-2(1H)-yl)-4-oxobutyric acid (intermediate VVV04) and 88.0 µl (0.61 mmol) of 3-trifluoromethyl benzylamine in DCM (15 ml) was cooled to 0° C. and then 8.3 mg (0.06 mmol) of HOAt and 129 mg (0.67 mmol) of EDC were added in succession. The mixture was then stirred for 16 h at room temperature. The reaction solution was poured into water (75 ml) and extracted with DCM (2×75 ml). The combined organic phases were washed with a 1M aqueous NaOH solution (100 ml) and brine, dried over Na$_2$SO$_4$, filtered and concentrated to small volume under vacuum. Column chromatography (heptane/EE 1:1+2% 7N NH$_3$ in MeOH) of the residue produced 240 mg (0.50 mmol, 81%) of 4-(7-fluoro-1-phenyl-3,4-dihydroisoquinolin-2(1H)-yl)-4-oxo-N-(3-(trifluoromethyl)benzyl)butyric acid amide. MS: m/z 485.2 [M+H]$^+$.

Synthesis of example compound 9: 4-(4-Methyl-1-phenyl-3,4-dihydro-1H-isoquinolin-2-yl)-4-oxo-N-[[3-(trifluoromethyl)phenyl]methyl]butyric acid amide 384 mg (2.0 mmol) of EDC, 306 µl (1.8 mmol) of DIPEA and 135 mg (1.0 mmol) of HOBt were added to a solution of 275 mg (1.0 mmol) of 4-oxo-4-(3-(trifluoromethyl)benzylamino)butyric acid (intermediate VVV01) in DCM (13 ml) and the mixture was stirred for 5 min at RT. Then 268 mg (1.2 mmol) of 4-methyl-1-phenyl-1,2,3,4-tetrahydroisoquinoline were added and the mixture was stirred for a further 2 h at RT. It was then diluted with DCM and washed successively with a 10% aqueous hydrochloric acid, a saturated aqueous Na$_2$CO$_3$ solution, a saturated aqueous NH$_4$Cl solution and brine. The organic phase was dried over Na$_2$SO$_4$, filtered and concentrated to small volume under vacuum. Column chromatography (hexane/EE 7:3) of the residue produced 346 mg (0.72 mmol, 72%) of 4-(4-methyl-1-phenyl-3,4-dihydro-1H-isoquinolin-2-yl)-4-oxo-N-[[3-(trifluoromethyl)phenyl]methyl]butyric acid amide. MS: m/z 481.2 [M+H]$^+$.

Automated Synthesis of Example Compounds 14-73

The correspondingly substituted 4-(3,4-dihydroisoquinolin-2(1H)-yl)-4-oxo-butyric acid derivative (100 µmol, 0.05 M in DCM (2 ml) or in a DCM/THF blend (3:1 vv, 2 ml)) was placed in a dry threaded glass jar sealed with a septum cover at RT and carbonyl diimidazole (105 µmol, 0.05 M in DCM (1 ml)) was added. After a reaction time of 1 h at RT the corresponding amine derivative (100 µmol, 0.1 M in DCM (1 ml)) was added at RT. After stirring for 16 h at RT the mixture was hydrolysed with water (3 ml), the reaction vessel drained and rinsed with DCM (2.5 ml). The phases were separated and the organic phase was washed again with water (3 ml) and then with brine (3 ml). The solvent was removed under vacuum and the products purified by HPLC. Analysis was performed by mass spectroscopy and the specified m/z (M+Hr found for all compounds.

Synthesis of Further Example Compounds

The synthesis of further example compounds took place by the methods already described. Table 2 shows which compound was prepared by which method. The starting materials and reagents used in each case are apparent to the person skilled in the art.

TABLE 2

| Example | Chemical name | Preparation analogous to example | Yield [%] | MS m/z [M + H]+ |
|---|---|---|---|---|
| 2 | 4-(1-Methyl-3,4-dihydro-1H-isoquinolin-2-yl)-4-oxo-N-[[3-(trifluoromethyl)phenyl]methyl]butyric acid amide | 1 | 38 | 405.2 |
| 4 | 4-Oxo-4-[1-(4-pyridyl)-3,4-dihydro-1H-isoquinolin-2-yl]-N-[[3-(trifluoromethyl)phenyl]methyl]butyric acid amide | 3 | 42 | 468.2 |
| 6 | 4-(5-Fluoro-1-phenyl-3,4-dihydro-1H-isoquinolin-2-yl)-4-oxo-N-[[3-(trifluoromethyl)phenyl]methyl]butyric acid amide | 5 | 92 | 485.2 |
| 7 | 4-Oxo-4-(1-phenyl-3,4-dihydro-1H-isoquinolin-2-yl)-N-[[2-(trifluoromethyl)phenyl]methyl]butyric acid amide | 3 | 55 | 467.2 |
| 8 | 4-Oxo-4-(1-phenyl-3,4-dihydro-1H-isoquinolin-2-yl)-N-[[4-(trifluoromethyl)phenyl]methyl]butyric acid amide | 3 | 68 | 467.2 |
| 10 | 4-(4,4-Dimethyl-1-phenyl-1,3-dihydroisoquinolin-2-yl)-4-oxo-N-[[3-(trifluoromethyl)phenyl]methyl]butyric acid amide | 9 | 49 | 495.2 |
| 11 | 4-(7-Methoxy-1-phenyl-3,4-dihydro-1H-isoquinolin-2-yl)-4-oxo-N-[[3-(trifluoromethyl)phenyl]methyl]butyric acid amide | 5 | 18 | 497.2 |
| 12 | 4-(5-Methoxy-1-phenyl-3,4-dihydro-1H-isoquinolin-2-yl)-4-oxo-N-[[3-(trifluoromethyl)phenyl]methyl]butyric acid amide | 5 | 14 | 497.2 |
| 13 | 4-(3-Methyl-1-phenyl-3,4-dihydro-1H-isoquinolin-2-yl)-4-oxo-N-[[3-(trifluoromethyl)phenyl]methyl]butyric acid amide | 5 | 52 | 481.2 |
| 14 | N-(2-Chlorophenyl)-4-oxo-4-(1-phenyl-3,4-dihydro-1H-isoquinolin-2-yl)butyric acid amide | 14-73 | N/A | 419.1 |
| 15 | N-(2,1,3-Benzothiadiazol-4-yl)-4-oxo-4-(1-phenyl-3,4-dihydro-1H-isoquinolin-2-yl)butyric acid amide | 14-73 | N/A | 443.1 |
| 16 | N-(1-Methyl-6-indazolyl)-4-oxo-4-(1-phenyl-3,4-dihydro-1H-isoquinolin-2-yl)butyric acid amide | 14-73 | N/A | 439.2 |
| 17 | N-(2-Furylmethyl)-4-oxo-4-(1-phenyl-3,4-dihydro-1H-isoquinolin-2-yl)butyric acid amide | 14-73 | N/A | 389.2 |
| 18 | N-Benzyl-4-oxo-4-(1-phenyl-3,4-dihydro-1H-isoquinolin-2-yl)butyric acid amide | 14-73 | N/A | 399.2 |
| 19 | 4-Oxo-4-(1-phenyl-3,4-dihydro-1H-isoquinolin-2-yl)-N-(2-pyridylmethyl)butyric acid amide | 14-73 | N/A | 400.2 |
| 20 | N-[(4-Methoxyphenyl)methyl]-4-oxo-4-(1-phenyl-3,4-dihydro-1H-isoquinolin-2-yl)butyric acid amide | 14-73 | N/A | 429.2 |
| 21 | 4-Oxo-N-phenethyl-4-(1-phenyl-3,4-dihydro-1H-isoquinolin-2-yl)butyric acid amide | 14-73 | N/A | 413.2 |
| 22 | 4-Oxo-4-(1-phenyl-3,4-dihydro-1H-isoquinolin-2-yl)-N-(4-pyridylmethyl)butyric acid amide | 14-73 | N/A | 400.2 |
| 23 | 4-Oxo-4-(1-phenyl-3,4-dihydro-1H-isoquinolin-2-yl)-N-(3-phenylpropyl)butyric acid amide | 14-73 | N/A | 427.2 |
| 24 | N-[2-(1H-Indol-3-yl)ethyl]-4-oxo-4-(1-phenyl-3,4-dihydro-1H-isoquinolin-2-yl)butyric acid amide | 14-73 | N/A | 452.2 |
| 25 | 4-(5,7-Dimethyl-1-phenyl-3,4-dihydro-1H-isoquinolin-2-yl)-N-(4-methoxyphenyl)-4-oxobutyric acid amide | 14-73 | N/A | 443.2 |
| 26 | N-(2-Chlorophenyl)-4-(5,7-dimethyl-1-phenyl-3,4-dihydro-1H-isoquinolin-2-yl)-4-oxobutyric acid amide | 14-73 | N/A | 447.2 |
| 27 | 4-(5,7-Dimethyl-1-phenyl-3,4-dihydro-1H-isoquinolin-2-yl)-N-(1-methyl-6-indazolyl)-4-oxobutyric acid amide | 14-73 | N/A | 467.2 |
| 28 | 4-(5,7-Dimethyl-1-phenyl-3,4-dihydro-1H-isoquinolin-2-yl)-N-(2-furylmethyl)-4-oxobutyric acid amide | 14-73 | N/A | 417.2 |
| 29 | N-Benzyl-4-(5,7-dimethyl-1-phenyl-3,4-dihydro-1H-isoquinolin-2-yl)-4-oxobutyric acid amide | 14-73 | N/A | 427.2 |
| 30 | 4-(5,7-Dimethyl-1-phenyl-3,4-dihydro-1H-isoquinolin-2-yl)-4-oxo-N-(2-pyridylmethyl)butyric acid amide | 14-73 | N/A | 428.2 |
| 31 | 4-(5,7-Dimethyl-1-phenyl-3,4-dihydro-1H-isoquinolin-2-yl)-N-[(4-methoxyphenyl)methyl]-4-oxobutyric acid amide | 14-73 | N/A | 457.2 |

TABLE 2-continued

| Example | Chemical name | Preparation analogous to example | Yield [%] | MS m/z [M + H]+ |
|---|---|---|---|---|
| 32 | 4-(5,7-Dimethyl-1-phenyl-3,4-dihydro-1H-isoquinolin-2-yl)-4-oxo-N-phenethylbutyric acid amide | 14-73 | N/A | 441.2 |
| 33 | 4-(5,7-Dimethyl-1-phenyl-3,4-dihydro-1H-isoquinolin-2-yl)-4-oxo-N-(3-phenylpropyl)butyric acid amide | 14-73 | N/A | 455.3 |
| 34 | N-(4-Methoxyphenyl)-4-(5-methyl-1-phenyl-3,4-dihydro-1H-isoquinolin-2-yl)-4-oxobutyric acid amide | 14-73 | N/A | 429.2 |
| 35 | N-(2-Chlorophenyl)-4-(5-methyl-1-phenyl-3,4-dihydro-1H-isoquinolin-2-yl)-4-oxobutyric acid amide | 14-73 | N/A | 433.2 |
| 36 | N-(1-Methyl-6-indazolyl)-4-(5-methyl-1-phenyl-3,4-dihydro-1H-isoquinolin-2-yl)-4-oxobutyric acid amide | 14-73 | N/A | 453.2 |
| 37 | N-(2-Furylmethyl)-4-(5-methyl-1-phenyl-3,4-dihydro-1H-isoquinolin-2-yl)-4-oxobutyric acid amide | 14-73 | N/A | 403.2 |
| 38 | N-Benzyl-4-(5-methyl-1-phenyl-3,4-dihydro-1H-isoquinolin-2-yl)-4-oxobutyric acid amide | 14-73 | N/A | 413.2 |
| 39 | 4-(5-Methyl-1-phenyl-3,4-dihydro-1H-isoquinolin-2-yl)-4-oxo-N-(2-pyridylmethyl)butyric acid amide | 14-73 | N/A | 414.2 |
| 40 | N-[(4-Methoxyphenyl)methyl]-4-(5-methyl-1-phenyl-3,4-dihydro-1H-isoquinolin-2-yl)-4-oxobutyric acid amide | 14-73 | N/A | 443.2 |
| 41 | 4-(5-Methyl-1-phenyl-3,4-dihydro-1H-isoquinolin-2-yl)-4-oxo-N-phenethylbutyric acid amide | 14-73 | N/A | 427.2 |
| 42 | 4-(5-Methyl-1-phenyl-3,4-dihydro-1H-isoquinolin-2-yl)-4-oxo-N-(3-phenylpropyl)butyric acid amide | 14-73 | N/A | 441.2 |
| 43 | N-(4-Methoxyphenyl)-4-(7-methyl-1-phenyl-3,4-dihydro-1H-isoquinolin-2-yl)-4-oxobutyric acid amide | 14-73 | N/A | 429.2 |
| 44 | N-(2-Chlorophenyl)-4-(7-methyl-1-phenyl-3,4-dihydro-1H-isoquinolin-2-yl)-4-oxobutyric acid amide | 14-73 | N/A | 433.2 |
| 45 | N-(1-Methyl-6-indazolyl)-4-(7-methyl-1-phenyl-3,4-dihydro-1H-isoquinolin-2-yl)-4-oxobutyric acid amide | 14-73 | N/A | 453.2 |
| 46 | N-(2-Furylmethyl)-4-(7-methyl-1-phenyl-3,4-dihydro-1H-isoquinolin-2-yl)-4-oxobutyric acid amide | 14-73 | N/A | 403.2 |
| 47 | N-Benzyl-4-(7-methyl-1-phenyl-3,4-dihydro-1H-isoquinolin-2-yl)-4-oxobutyric acid amide | 14-73 | N/A | 413.2 |
| 48 | 4-(7-Methyl-1-phenyl-3,4-dihydro-1H-isoquinolin-2-yl)-4-oxo-N-(2-pyridylmethyl)butyric acid amide | 14-73 | N/A | 414.2 |
| 49 | N-[(4-Methoxyphenyl)methyl]-4-(7-methyl-1-phenyl-3,4-dihydro-1H-isoquinolin-2-yl)-4-oxobutyric acid amide | 14-73 | N/A | 443.2 |
| 50 | 4-(7-Methyl-1-phenyl-3,4-dihydro-1H-isoquinolin-2-yl)-4-oxo-N-phenethylbutyric acid amide | 14-73 | N/A | 427.2 |
| 51 | 4-(7-Methyl-1-phenyl-3,4-dihydro-1H-isoquinolin-2-yl)-4-oxo-N-(4-pyridylmethyl)butyric acid amide | 14-73 | N/A | 414.2 |
| 52 | 4-Oxo-4-(1-phenyl-3,4-dihydro-1H-isoquinolin-2-yl)-N-(2-thienylmethyl)butyric acid amide | 14-73 | N/A | 405.2 |
| 53 | N-[(2-Chlorophenyl)methyl]-4-oxo-4-(1-phenyl-3,4-dihydro-1H-isoquinolin-2-yl)butyric acid amide | 14-73 | N/A | 433.2 |
| 54 | N-[(2,4-Dichlorophenyl)methyl]-4-oxo-4-(1-phenyl-3,4-dihydro-1H-isoquinolin-2-yl)butyric acid amide | 14-73 | N/A | 467.1 |
| 55 | N-[(3,4-Dichlorophenyl)methyl]-4-oxo-4-(1-phenyl-3,4-dihydro-1H-isoquinolin-2-yl)butyric acid amide | 14-73 | N/A | 467.1 |
| 56 | 4-Oxo-4-(1-phenyl-3,4-dihydro-1H-isoquinolin-2-yl)-N-(p-tolylmethyl)butyric acid amide | 14-73 | N/A | 413.2 |
| 57 | N-(1,3-Benzodioxol-5-ylmethyl)-4-oxo-4-(1-phenyl-3,4-dihydro-1H-isoquinolin-2-yl)butyric acid amide | 14-73 | N/A | 443.2 |

TABLE 2-continued

| Example | Chemical name | Preparation analogous to example | Yield [%] | MS m/z [M + H]+ |
|---|---|---|---|---|
| 58 | N-[(3-Fluorophenyl)methyl]-4-oxo-4-(1-phenyl-3,4-dihydro-1H-isoquinolin-2-yl)butyric acid amide | 14-73 | N/A | 417.2 |
| 59 | N-[(2-Fluorophenyl)methyl]-4-oxo-4-(1-phenyl-3,4-dihydro-1H-isoquinolin-2-yl)butyric acid amide | 14-73 | N/A | 417.2 |
| 60 | N-[(4-Fluorophenyl)methyl]-4-oxo-4-(1-phenyl-3,4-dihydro-1H-isoquinolin-2-yl)butyric acid amide | 14-73 | N/A | 417.2 |
| 61 | N-[(2,5-Difluorophenyl)methyl]-4-oxo-4-(1-phenyl-3,4-dihydro-1H-isoquinolin-2-yl)butyric acid amide | 14-73 | N/A | 435.2 |
| 62 | N-(1-Naphthylmethyl)-4-oxo-4-(1-phenyl-3,4-dihydro-1H-isoquinolin-2-yl)butyric acid amide | 14-73 | N/A | 449.2 |
| 63 | 4-(7-Methyl-1-phenyl-3,4-dihydro-1H-isoquinolin-2-yl)-4-oxo-N-propylbutyric acid amide | 14-73 | N/A | 365.2 |
| 64 | 4-(5-Methyl-1-phenyl-3,4-dihydro-1H-isoquinolin-2-yl)-4-oxo-N-propylbutyric acid amide | 14-73 | N/A | 365.2 |
| 65 | 4-(5,7-Dimethyl-1-phenyl-3,4-dihydro-1H-isoquinolin-2-yl)-4-oxo-N-propylbutyric acid amide | 14-73 | N/A | 379.2 |
| 66 | 4-Oxo-4-(1-phenyl-3,4-dihydro-1H-isoquinolin-2-yl)-N-propylbutyric acid amide | 14-73 | N/A | 351.2 |
| 67 | 4-Oxo-4-(1-(2-tolyl)-3,4-dihydro-1H-isoquinolin-2-yl)-N-[[3-(trifluoromethyl)phenyl]methyl]butyric acid amide | 14-73 | 54 | 481.2 |
| 68 | 4-Oxo-4-(1-(2-tolyl)-3,4-dihydro-1H-isoquinolin-2-yl)-N-[[4-(trifluoromethyl)phenyl]methyl]butyric acid amide | 14-73 | 51 | 481.2 |
| 69 | 4-Oxo-4-(1-(2-tolyl)-3,4-dihydro-1H-isoquinolin-2-yl)-N-[[2-(trifluoromethyl)phenyl]methyl]butyric acid amide | 14-73 | 59 | 481.2 |
| 70 | 4-Oxo-4-(1-(2-tolyl)-6-methyl-3,4-dihydro-1H-isoquinolin-2-yl)-N-[[3-(trifluoromethyl)phenyl]methyl]butyric acid amide | 14-73 | N/A | 495.2 |
| 71 | 4-(1-(2-Methyl-prop-2-yl)-3,4-dihydro-1H-isoquinolin-2-yl)-4-oxo-N-[[3-trifluoromethyl)phenyl]methyl]butyric acid amide | 14-73 | N/A | 447.2 |
| 72 | 4-(1-Cyclohexyl-3,4-dihydro-1H-isoquinolin-2-yl)-4-oxo-N-[[3-(trifluoromethyl)phenyl]methyl]butyric acid amide | 14-73 | N/A | 473.2 |
| 73 | 4-Oxo-4-(1-(2-fluorophenyl)-3,4-dihydro-1H-isoquinolin-2-yl)-N-[[3-(trifluoromethyl)phenyl]methyl]butyric acid amide | 14-73 | N/A | 485.2 |

Pharmacological Experiments
Fluorescence Assay Using a Voltage-Sensitive Dye

Human CHO-K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% foetal calf serum (FCS) (Invitrogen, #10270-106, heat-inactivated) and the necessary selection antibiotics.

Before being sown out for the measurements, the cells are washed with a 1×DPBS buffer without $Ca^{2+}/Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Scharfe System) in order subsequently to apply 20,000 to 30,000 cells/well/100 µl of the described nutrient medium, depending on density optimisation for the individual cell line, to 96-well measuring plates of the Corning™ CellBIND™ type (flat clear-bottom black polystyrene microplates, #3340).

Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red™ bulk format part R8123 for FLIPR, MDS Analytical Technologies™) is prepared by dissolving the contents of a vessel of Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 µl of ES buffer, then covered with a layer of 100 µl of the dye solution prepared above and incubated for 45 min at room temperature with exclusion of light.

The fluorescence measurements are carried out with a BMG Labtech FLUOstar™ BMG Labtech NOVOstar™ or BMG Labtech POLARstar™ instrument (525 nm excitation, 560 nm emission, bottom-read mode). After incubation of the dye, 50 µl of the substances to be tested in the desired concentrations, or 50 µl of ES buffer for control purposes, are introduced into separate cavities of the measuring plate and incubated for 30 min at room temperature whilst being shielded from light. The fluorescence intensity of the dye is then measured for 5 min and the fluorescence value $F_1$ of each well is thus determined at a given, constant time. 15 µl of a 100 mM KCl solution (final concentration 92 mM) are then added to each well. The change in fluorescence is subsequently measured until all relevant measured values have been obtained (mainly 5-30 min). At a given time after KCl application, a fluorescence value $F_2$ is determined, in this case at the time of the fluorescence peak.

For calculation, the fluorescence intensity $F_2$ is compared with the fluorescence intensity $F_1$, and the agonistic activity of the target compound on the potassium channel is determined therefrom. $F_2$ and $F_1$ are calculated as follows:

$$\left(\frac{F_2 - F_1}{F_1}\right) \times 100 = \frac{\Delta F}{F} (\%)$$

In order to determine whether a substance has an agonistic activity, $$\frac{\Delta F}{F},$$

for example, can be compared with $$\left(\frac{\Delta F}{F}\right)_K$$

of control cells.

$$\left(\frac{\Delta F}{F}\right)_K$$

is determined by adding to the reaction batch only the buffer solution instead of the substance to be tested, determining the value $F_{1K}$ of the fluorescence intensity, adding the potassium ions as described above and measuring a value $F_{2K}$ of the fluorescence intensity. Then $F_{2K}$ and $F_{1K}$ are calculated as follows:

$$\left(\frac{F_{2K} - F_{1K}}{F_{1K}}\right) \times 100 = \left(\frac{\Delta F}{F}\right)_K (\%)$$

A substance has an agonistic activity on the potassium channel if $$\frac{\Delta F}{F}$$

is greater than $$\left(\frac{\Delta F}{F}\right)_K : \frac{\Delta F}{F} \left(\frac{\Delta F}{F}\right)_K$$

Independently of the comparison of $$\frac{\Delta F}{F} \text{ with } \left(\frac{\Delta F}{F}\right)_K,$$

it is also possible to conclude that a target compound has an agonistic activity if an increase in $$\frac{\Delta F}{F}$$

is to be observed as the dosage of the target compound increases.

Calculations of $EC_{50}$ and $IC_{50}$ values are carried out with the aid of Prism v4.0 software (GraphPad Software™).

Voltage-Clamp Measurements

In order to confirm a KCNQ2/3 agonistic action of the substances electrophysiologically, patch-clamp measurements (Hamill O P, Marty A, Neher E, Sakmann B, Sigworth F J: Improved patch-clamp techniques for high-resolution current recording from cells and cell-free membrane patches, Pfluger's Arch. 1981 August; 391(2):85-100) were performed in voltage-clamp mode on a stably transfected hKCNQ2/3 CHO-K1 cell line. After formation of the gigaseal the cells were first clamped at a holding potential of −60 mV. Depolarising voltage jumps up to a potential of +20 mV were then applied (increment: 20 mV, duration: 1 second) in order to confirm the functional expression of KCNQ2/3-typical currents. The substances were tested at a potential of −40 mV. First of all the current increase induced by retigabine (10 µM) at −40 mV was recorded on each cell as a positive control. After completely washing out the retigabine effect (duration: 80 s) the test substance (10 µM) was applied. The current increase induced by the test substance was normalised against the retigabine effect and stated as the relative efficacy (see below).

Formalin Test in the Rat

The formalin test (Dubuisson, D. and Dennis, S. G., 1977, Pain, 4, 161-174) is a model for acute and chronic pain. In the tests described here, the chronic pain component (phase II of the formalin test; time interval 21-27 min after formalin administration) was analysed.

A single formalin injection into the dorsal side of one rear paw was used to induce a biphase nociceptive response in experimental animals allowed to move freely, and the response was recorded by observation of three clearly distinguishable behaviour patterns.

Formalin is administered subcutaneously in a volume of 50 µl and a concentration of 5% into the dorsal side of the right rear paw of each animal. The vehicle and the substances to be tested are administered intravenously 5 minutes before or orally 30 minutes before the formalin injection.

The specific behavioural changes, such as lifting and shaking the paw, shifting of weight by the animal and biting and licking responses, are observed and recorded continuously for 60 minutes after formalin administration. The behavioural changes are weighted differently (score 0-3) and a pain rate (PR) calculated using the formula below:

$PR = [(T_0 \times 0) + (T_1 \times 1) + (T_2 \times 2) + (T_3 \times 3)]/180$.

$T_0$, $T_1$, $T_2$, $T_3$ each correspond to the time in seconds for which the animal displayed behaviours 0, 1, 2 or 3.

Sprague Dawley rats (Janvier, Belgium) are used as the phylum. The weight of the animals is between 180 and 200 g. The group size was n=10.

Pharmacological Data

The results of the pharmacological models described above are summarised in Table 3.

TABLE 3

| Example compound | Fluorimetry % Efficacy @ 10 μM (Retigabine = 100%) | Fluorimetry % Efficacy @ 1 μM (Retigabine = 100%) | Fluorimetry $EC_{50}$ [μM] | Patch-clamp % Efficacy @ 10 μM (Retigabine = 100%) | Formalin test rat i.v. @ 4.64 mg/kg % Reduction of nociceptive behaviour [%] |
|---|---|---|---|---|---|
| 1 | 110 | | 1.90 | 78 | 40 |
| 2 | | | 10.4 | 17 | |
| 3 | 134 | 76 | 1.05 | | |
| 4 | 35 | 11 | | | |
| 5 | | 69 | 0.083 | | |
| 6 | | 73 | 0.075 | | |
| 7 | | 12 | | | |
| 8 | | 63 | | | |
| 9 | | 51 | 0.116 | | |
| 10 | | 45 | 0.135 | | |
| 11 | | 30 | | | |
| 12 | | −7 | | | |
| 13 | | 29 | | | |
| 67 | | 112 | 0.215 | | |
| 68 | | 56 | 0.149 | | |
| 69 | | 67 | 0.158 | | |

Comparative Experiments

The substituted tetrahydroisoquinolinyl-4-oxobutyric acid amides according to the invention are characterised by an improved efficacy in vitro and in vivo as compared with substituted tetrahydropyrrolopyrazines known from WO 2008/046582, as the comparative experiments below illustrate:

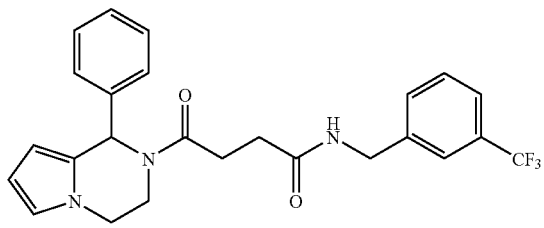

Example no. 2 in WO2008/046582

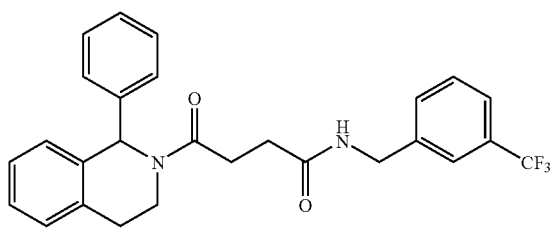

Compound 1 according to the invention

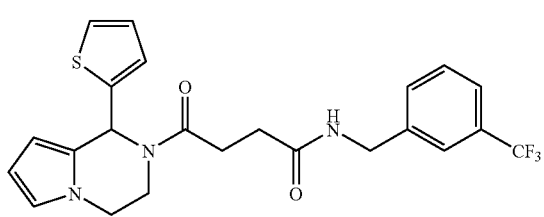

Example no. 76 in WO2008/046582

-continued

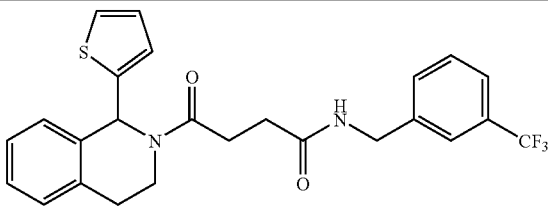

Compound 3 according to the invention

| | Fluorimetry % Efficacy @ 10 μM (Retigabine = 100%) | Fluorimetry $ED_{50}$ [μM] | Formalin test rat i.v. @ 4.64 mg/kg % Reduction of nociceptive behaviour [%] |
|---|---|---|---|
| Example no. 2 in WO2008/046582 | 115 | 2.81 | No effect |
| 1 | 110 | 1.90 | 40 |
| Example no. 76 in WO2008/046582 | 113 | 3.29 | Not tested |
| 3 | 134 | 1.05 | Not tested |

The invention claimed is:
1. A substituted tetrahydroisoquinolinyl-4-oxobutyric acid amide compound having the formula (1),

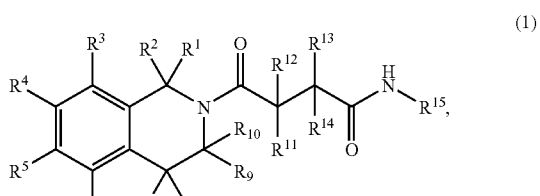

wherein
$R^0$ stands for $C_{1-10}$ alkyl or $C_{2-10}$ heteroalkyl, each saturated or unsaturated, branched or unbranched, unsubstituted or mono- or polysubstituted; $C_{3-7}$ cycloalkyl or heterocyclyl, each saturated or unsaturated, unsubstituted or mono- or polysubstituted; aryl or heteroaryl, each unsubstituted or mono- or polysubstituted; $C_{1-8}$ alkyl-bridged $C_{3-7}$ cycloalkyl or heterocyclyl, each saturated or unsaturated, unsubstituted or mono- or polysubstituted, wherein the alkyl chain can in each case be branched or unbranched, saturated or unsaturated, unsubstituted, mono- or polysubstituted; or $C_{1-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted;

$R^1$ stands for F; Cl; Br; CN; $C_{1-10}$ alkyl or $C_{2-10}$ heteroalkyl, each saturated or unsaturated, branched or unbranched, unsubstituted or mono- or polysubstituted; $C_{3-7}$ cycloalkyl or heterocyclyl, each saturated or unsaturated, unsubstituted or mono- or polysubstituted; aryl or heteroaryl, each unsubstituted or mono- or polysubstituted; $C_{1-8}$ alkyl-bridged $C_{3-7}$ cycloalkyl or heterocyclyl, each saturated or unsaturated, unsubstituted or mono- or polysubstituted, wherein the alkyl chain can in each case be branched or unbranched, saturated or unsaturated, unsubstituted, mono- or polysubstituted; $C_{1-8}$ alkyl-bridged heteroaryl, unsubstituted or mono- or polysubstituted, wherein the alkyl chain can be branched or unbranched, saturated or unsaturated, unsubstituted, mono- or polysubstituted; or $C_{1-8}$ alkyl-bridged aryl, unsubstituted or mono- or polysubstituted, wherein the alkyl chain can be unbranched, saturated or unsaturated, unsubstituted;

$R^2$ stands for H; F; Cl; Br; or $C_{1-10}$ alkyl, saturated or unsaturated, branched or unbranched, unsubstituted or mono- or polysubstituted;

or $R^1$ and $R^2$ together with the carbon atom binding them as ring member form a $C_{3-7}$ cycloalkyl or heterocyclyl, each saturated or unsaturated, unsubstituted or mono- or polysubstituted, each optionally fused to (hetero)aryl, unsubstituted or mono- or polysubstituted;

$R^3$, $R^4$, $R^5$ and $R^6$ each mutually independently denote H; F; Cl; Br; I; $NO_2$; $CF_3$; CN; $R^0$; C(=O)H; C(=O)$R^0$; $CO_2H$; C(=O)$OR^0$; $CONH_2$; C(=O)$NHR^0$; C(=O)$N(R^0)_2$; OH; $OR^0$; —O—($C_{1-8}$ alkyl)-O—; O—C(=O)—$R^0$; O—C(=O)—O—$R^0$; O—(C=O)—NH—$R^0$; O—C(=O)—$N(R^0)_2$; O—S(=O)$_2$—$R^0$; O—S(=O)$_2$OH; O—S(=O)$_2OR^0$; O—S(=O)$_2NH_2$; O—S(=O)$_2NHR^0$; O—S(=O)$_2N(R^0)_2$; $NH_2$; NH—$R^0$; $N(R^0)_2$; NH—C(=O)—$R^0$; NH—C(=O)—O—$R^0$; NH—C(=O)—$NH_2$; NH—C(=O)—NH—$R^0$; NH—C(=O)—) $N(R^0)_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—) $N(R^0)_2$; NH—S(=O)$_2$OH; NH—S(=O)$_2R^0$; NH—S(=O)$_2OR^0$; NH—S(=O)$_2NH_2$; NH—S(=O)$_2NHR^0$; NH—S(=O)$_2N(R^0)_2$; $NR^0$—S(=O)$_2$OH; $NR^0$—S(=O)$_2R^0$; $NR^0$—S(=O)$_2OR^0$; $NR^0$—S(=O)$_2NH_2$; $NR^0$—S(=O)$_2NHR^0$; $NR^0$—S(=O)$_2N(R^0)_2$; SH; $SR^0$; S(=O)$R^0$; S(=O)$_2R^0$; S(=O)$_2$OH; S(=O)$_2OR^0$; S(=O)$_2NH_2$; S(=O)$_2NHR^0$; or S(=O)$_2N(R^0)_2$;

$R^7$, $R^8$, $R^9$, $R^{10}$ each mutually independently stand for H; F; Cl; Br; or $C_{1-10}$ alkyl, saturated or unsaturated, branched or unbranched, unsubstituted or mono- or polysubstituted;

$R^{11}$ stands for H; F; Cl; Br; CN; or $R^0$;

$R^{12}$ stands for H; F; Cl; Br; CN; or $C_{1-10}$ alkyl, saturated or unsaturated, branched or unbranched, unsubstituted or mono- or polysubstituted;

$R^{13}$ stands for H; F; Cl; Br; CN; $C_{1-10}$ alkyl or $C_{2-10}$ heteroalkyl, each saturated or unsaturated, branched or unbranched, unsubstituted or mono- or polysubstituted; $C_{3-7}$ cycloalkyl or heterocyclyl, each saturated, unsubstituted or mono- or polysubstituted; aryl or heteroaryl, each unsubstituted or mono- or polysubstituted; $C_{1-8}$ alkyl-bridged $C_{3-7}$ cycloalkyl or heterocyclyl, each saturated or unsaturated, unsubstituted or mono- or polysubstituted, wherein the alkyl chain can in each case be branched or unbranched, saturated or unsaturated, unsubstituted, mono- or polysubstituted; or $C_{2-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted;

$R^{14}$ stands for H; F; Cl; Br; CN; or $C_{1-10}$ alkyl, saturated or unsaturated, branched or unbranched, unsubstituted or mono- or polysubstituted;

or $R^{11}$ and $R^{13}$ together with the carbon atoms binding them as ring members form a $C_{3-7}$ cycloalkyl or heterocyclyl, each saturated or unsaturated, unsubstituted or mono- or polysubstituted, optionally fused to (hetero)aryl, unsubstituted or mono- or polysubstituted;

or $R^{11}$ and $R^{12}$; or $R^{13}$ and $R^{14}$, together with the carbon atoms binding them as ring members form a $C_{3-7}$ cycloalkyl or heterocyclyl, each saturated or unsaturated, unsubstituted or mono- or polysubstituted, each optionally fused to (hetero)aryl, unsubstituted or mono- or polysubstituted;

$R^{15}$ stands for $R^0$;

wherein "alkyl-substituted", "heteroalkyl-substituted", "heterocyclyl-substituted" and "cycloalkyl-substituted" stand for the substitution of one or more hydrogen atoms, each mutually independently, with F; Cl; Br; I; CN; $CF_3$; =O; =NH; =C(NH$_2$)$_2$; $NO_2$; $R^0$; C(=O)H; C(=O)$R^0$; $CO_2H$; C(=O)$OR^0$; $CONH_2$; C(=O)$NHR^0$; C(=O)$N(R^0)_2$; OH; $OR^0$; O—($C_{1-8}$ alkyl)-O; O—C(=O)—$R^0$; O—C(=O)—O—$R^0$; O—(C=O)—NH—$R^0$; O—C(=O)—$N(R^0)_2$; O—S(=O)$_2$—$R^0$; O—S(=O)$_2$OH; O—S(=O)$_2OR^0$; O—S(=O)$_2NH_2$; O—S(=O)$_2NHR^0$; O—S(=O)$_2N(R^0)_2$; $NH_2$; NH—$R^0$; $N(R^0)_2$; NH—C(=O)—$R^0$; NH—C(=O)—O—$R^0$; NH—C(=O)—$NH_2$; NH—C(=O)—NH—$R^0$; NH—C(=O)—$N(R^0)_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—$N(R^0)_2$; NH—S(=O)$_2$OH; NH—S(=O)$_2R^0$; NH—S(=O)$_2OR^0$; NH—S(=O)$_2NH_2$; NH—S(=O)$_2NHR^0$; NH—S(=O)$_2N(R^0)_2$; $NR^0$—S(=O)$_2$OH; $NR^0$—S(=O)$_2R^0$; $NR^0$—S(=O)$_2OR^0$; $NR^0$—S(=O)$_2NH_2$; $NR^0$—S(=O)$_2NHR^0$; $NR^0$—) S(=O)$_2N(R^0)_2$; SH; $SR^0$; S(=O)$R^0$; S(=O)$_2R^0$; S(=O)$_2$OH; S(=O)$_2OR^0$; S(=O)$_2NH_2$; S(=O)$_2NHR^0$; or S(=O)$_2N(R^0)_2$;

wherein "aryl-substituted" and "heteroaryl-substituted" stand for the substitution of one or more hydrogen atoms, each mutually independently, with F; Cl; Br; I; $NO_2$; $CF_3$; CN; $R^0$; C(=O)H; C(=O)$R^0$; $CO_2H$; C(=O)$OR^0$; $CONH_2$; C(=O)$NHR^0$; C(=O)$N(R^0)_2$; OH; $OR^0$; O—($C_{1-8}$ alkyl)-O; O—C(=O)—$R^0$; O—C(=O)—O—$R^0$; O—(C=O)—NH—$R^0$; O—C(=O)—$N(R^0)_2$; O—S(=O)$_2$—$R^0$; O—S(=O)$_2$OH; O—S(=O)$_2OR^0$; O—S(=O)$_2NH_2$; O—S(=O)$_2NHR^0$; O—S(=O)$_2N(R^0)_2$; $NH_2$; NH—$R^0$; $N(R^0)_2$; NH—C(=O)—$R^0$; NH—C(=O)—O—$R^0$; NH—C(=O)—$NH_2$; NH—C(=O)—NH—$R^0$; NH—C(=O)—$N(R^0)_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—$N(R^0)_2$; NH—S(=O)$_2$OH; NH—S(=O)$_2R^0$; NH—S(=O)$_2OR^0$; NH—S(=O)$_2NH_2$; NH—S(=O)$_2NHR^0$; NH—) S(=O)$_2N(R^0)_2$; $NR^0$—S(=O)$_2$OH; $NR^0$—S (=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; SR$^0$; S(=O)R$^0$; S(=O)$_2$R$^0$; S(=O)$_2$OH; S(=O)$_2$OR$^0$; S(=O)$_2$NH$_2$; S(=O)$_2$NHR$^0$; or S(=O)$_2$N(R$^0$)$_2$; said compound being present in the form of an individual stereoisomer or a mixture thereof, a free compound and/or a salt of a physiologically compatible acid or base.

2. A compound as claimed in claim 1, wherein
R$^1$ stands for C$_{1-10}$ alkyl or C$_{2-10}$ heteroalkyl, each saturated or unsaturated, branched or unbranched, unsubstituted or mono- or polysubstituted; C$_{3-7}$ cycloalkyl, saturated or unsaturated, unsubstituted or mono- or polysubstituted; aryl or heteroaryl, each unsubstituted or mono- or polysubstituted; C$_{1-8}$ alkyl-bridged C$_{3-7}$ cycloalkyl, saturated or unsaturated, unsubstituted or mono- or polysubstituted, wherein the alkyl chain can be branched or unbranched, saturated or unsaturated, unsubstituted, mono- or polysubstituted; C$_{1-8}$ alkyl-bridged heteroaryl, unsubstituted or mono- or polysubstituted, wherein the alkyl chain can be branched or unbranched, saturated or unsaturated, unsubstituted, mono- or polysubstituted; or C$_{1-8}$ alkyl-bridged aryl, unsubstituted or mono- or polysubstituted, wherein the alkyl chain can be unbranched, saturated or unsaturated, unsubstituted;
R$^2$ stands for H; or C$_{1-10}$ alkyl, saturated or unsaturated, branched or unbranched, unsubstituted or mono- or polysubstituted.

3. A compound as claimed in claim 1, wherein
R$^3$, R$^4$, R$^5$ and R$^6$ each mutually independently denote H; F; Cl; Br; I; NO$_2$; CF$_3$; CN; R$^0$; C(=O)(R$^0$ or H); C(=O)O(R$^0$ or H); C(=O)N(R$^0$ or H)$_2$; OH; OR$^0$; —O—(C$_{1-8}$ alkyl)-O—; O—(C$_{1-8}$ alkyl)-O—C$_{1-8}$ alkyl; OCF$_3$; N(R$^0$ or H)$_2$; N(R$^0$ or H)—C(=O)—R$^0$; N(R$^0$ or H)—C(=O)—N(R$^0$ or H)$_2$; SH; SCF$_3$; SR$^0$; S(=O)$_2$R$^0$; S(=O)$_2$O(R$^0$ or H); S(=O)$_2$—N(R$^0$ or H)$_2$.

4. A compound as claimed in claim 1, wherein
R$^7$, R$^8$, R$^9$, R$^{10}$ mutually independently stand for H; or C$_{1-10}$ alkyl, saturated or unsaturated, branched or unbranched, unsubstituted or mono- or polysubstituted.

5. A compound as claimed in claim 1, wherein
R$^{11}$ stands for H; F; Cl; Br; CN; C$_{1-10}$ alkyl, saturated or unsaturated, branched or unbranched, unsubstituted or mono- or polysubstituted; phenyl or heteroaryl, each unsubstituted or mono- or polysubstituted; or C$_{1-4}$ alkyl-bridged phenyl or heteroaryl, each unsubstituted or mono- or polysubstituted, wherein the alkyl chain can in each case be branched or unbranched, saturated or unsaturated, unsubstituted or mono- or polysubstituted;
R$^{13}$ stands for H; F; Cl; Br; CN; C$_{1-10}$ alkyl, saturated or unsaturated, branched or unbranched, unsubstituted or mono- or polysubstituted; phenyl or heteroaryl, each unsubstituted or mono- or polysubstituted; or C$_{2-4}$ alkyl-bridged phenyl or heteroaryl, each unsubstituted or mono- or polysubstituted, wherein the alkyl chain can in each case be branched or unbranched, saturated or unsaturated, unsubstituted or mono- or polysubstituted;
or R$^{11}$ and R$^{13}$ together with the carbon atoms binding them as ring members form a C$_{3-7}$ cycloalkyl or heterocyclyl, each saturated or unsaturated, unsubstituted or mono- or polysubstituted, optionally fused to phenyl, unsubstituted or mono- or polysubstituted.

6. A compound as claimed in claim 1, wherein
R$^{12}$ and R$^{14}$ each mutually independently stand for H; or C$_{1-10}$ alkyl, saturated or unsaturated, branched or unbranched, unsubstituted or mono- or polysubstituted.

7. A compound as claimed in claim 1, wherein
R$^{15}$ stands for C$_{3-10}$ alkyl or C$_{2-10}$ heteroalkyl, each saturated or unsaturated, branched or unbranched, unsubstituted or mono- or polysubstituted; C$_{3-7}$ cycloalkyl, saturated or unsaturated, unsubstituted or mono- or polysubstituted; aryl or heteroaryl, unsubstituted or mono- or polysubstituted; C$_{1-8}$ alkyl-bridged C$_{3-7}$ cycloalkyl, saturated or unsaturated, unsubstituted or mono- or polysubstituted, wherein the alkyl chain can in each case be branched or unbranched, saturated or unsaturated, unsubstituted, mono- or polysubstituted; or C$_{1-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted.

8. A compound as claimed in claim 1, having the formula (2),

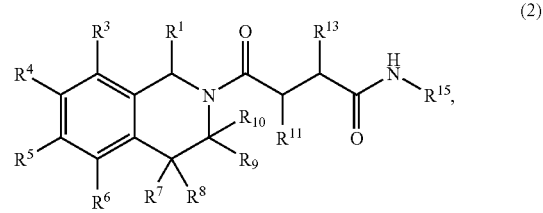

wherein
R$^1$ stands for C$_{1-10}$ alkyl or C$_{2-10}$ heteroalkyl, each saturated or unsaturated, branched or unbranched, unsubstituted or mono- or polysubstituted; C$_{3-7}$ cycloalkyl, saturated or unsaturated, unsubstituted or mono- or polysubstituted; phenyl or thienyl, each unsubstituted or mono- or polysubstituted; C$_{1-8}$ alkyl-bridged C$_{3-7}$ cycloalkyl, saturated or unsaturated, unsubstituted or mono- or polysubstituted; C$_{1-8}$ alkyl-bridged phenyl, unsubstituted or mono- or polysubstituted, wherein the alkyl chain can be branched or unbranched, saturated or unsaturated, unsubstituted; or C$_{1-8}$ alkyl-bridged thienyl, unsubstituted or mono- or polysubstituted, wherein the alkyl chain can be branched or unbranched, saturated or unsaturated, unsubstituted or mono- or polysubstituted;
R$^3$, R$^4$, R$^5$ and R$^6$ each mutually independently denote H; F; Cl; Br; I; NO$_2$; CF$_3$; CN; R$^0$; C(=O)(R$^0$ or H); C(=O)O(R$^0$ or H); C(=O)N(R$^0$ or H)$_2$; OH; OR$^0$; O—(C$_{1-8}$ alkyl)-O; O—(C$_{1-8}$ alkyl)-O—C$_{1-8}$ alkyl; N(R$^0$ or H)$_2$; N(R$^0$ or H)—C(=O)—R$^0$; N(R$^0$ or H)—C(=O)—N(R$^0$ or H)$_2$; SH; SR$^0$; S(=O)$_2$R$^0$; S(=O)$_2$O(R$^0$ or H); or S(=O)$_2$—N(R$^0$ or H)$_2$;
R$^7$, R$^8$, R$^9$, R$^{10}$ each mutually independently stand for H; or C$_{1-4}$ alkyl, saturated or unsaturated, branched or unbranched, unsubstituted or mono- or polysubstituted;
R$^{11}$ and R$^{13}$ each independently stand for H; or C$_{1-10}$ alkyl, saturated or unsaturated, branched or unbranched, unsubstituted or mono- or polysubstituted;
or R$^{11}$ and R$^{13}$ together with the carbon atoms binding them as ring members form a C$_{3-7}$ cycloalkyl or heterocyclyl, each saturated or unsaturated, unsubstituted or mono- or polysubstituted;
R$^{15}$ stands for C$_{3-10}$ alkyl, saturated or unsaturated, branched or unbranched, unsubstituted or mono- or polysubstituted; C$_{3-7}$ cycloalkyl, saturated or unsaturated, unsubstituted or mono- or polysubstituted; aryl or heteroaryl, unsubstituted or mono- or polysubstituted; $C_{1-8}$ alkyl-bridged $C_{3-7}$ cycloalkyl, saturated or unsaturated, unsubstituted or mono- or polysubstituted, wherein the alkyl chain can in each case be branched or unbranched, saturated or unsaturated, unsubstituted, mono- or polysubstituted; or $C_{1-8}$ alkyl-bridged aryl or heteroaryl, each unsubstituted or mono- or polysubstituted, wherein the alkyl chain can in each case be branched or unbranched, saturated or unsaturated, unsubstituted, mono- or polysubstituted.

9. A compound as claimed in claim 1, wherein
$R^{15}$ stands for $C_{3-10}$ alkyl, saturated or unsaturated; branched or unbranched, unsubstituted or mono- or polysubstituted; or is selected from the following substructures A, B or C,

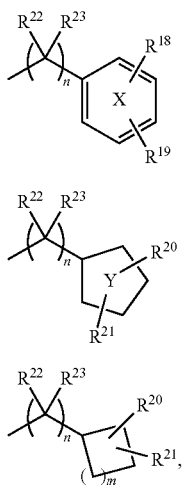

wherein
n=0, 1, 2, 3, 4, 5, 6, 7 or 8;
m=0, 1, 2 or 3;
ring X can contain one or two N atoms as ring member(s);
ring Y contains at least 1 heteroatom selected from N, O or S and can contain up to 3 heteroatoms mutually independently selected from N, O or S; and/or can contain one or two double bonds;
$R^{18}$ and $R^{19}$ mutually independently denote H; F; Cl; Br; I; $NO_2$; $CF_3$; CN; $R^0$; C(=O)($R^0$ or H); C(=O)O($R^0$ or H); C(=O)N($R^0$ or H)$_2$; OH; $OR^0$; $OR^0$; O—($C_{1-8}$ alkyl)-O; O—($C_{1-8}$ alkyl)-O—$C_{1-8}$ alkyl; N($R^0$ or H)$_2$; N($R^0$ or H)—C(=O)—$R^0$; N($R^0$ or H)—C(=O)—N($R^0$ or H)$_2$; SH; $SR^0$; S(=O)$_2R^0$; S(=O)$_2$O($R^0$ or H); or S(=O)$_2$—N($R^0$ or H)$_2$H;
or $R^{18}$ and $R^{19}$ together with the carbon or nitrogen atoms binding them as ring members form an aryl or heteroaryl fused to the phenyl or heteroaryl ring, each unsubstituted or mono- or polysubstituted; or a $C_{3-7}$ cycloalkyl or heterocyclyl fused to the phenyl or heteroaryl ring, each saturated or unsaturated, unsubstituted or mono- or polysubstituted;
$R^{20}$ and $R^{21}$ mutually independently denote H or $C_{1-10}$ alkyl, saturated or unsaturated; branched or unbranched, unsubstituted or mono- or polysubstituted; or $C_{3-7}$ cycloalkyl or heterocyclyl, each saturated or unsaturated, unsubstituted or mono- or polysubstituted;
or $R^{20}$ and $R^{21}$ together with the carbon atoms or heteroatoms binding them as ring members form an aryl or heteroaryl fused to ring Y, each unsubstituted or mono- or polysubstituted;
$R^{22}$ and $R^{23}$ mutually independently denote H; or $C_{1-10}$ alkyl, saturated or unsaturated; branched or unbranched, unsubstituted.

10. A compound as claimed in claim 1, selected from the group consisting of:
4-Oxo-4-(1-phenyl-3,4-dihydroisoquinolin-2(1H)-yl)-N-(3-(trifluoromethyl)benzyl)butyric acid amide;
4-(1-Methyl-3,4-dihydro-1H-isoquinolin-2-yl)-4-oxo-N-[[3-(trifluoromethyl)phenyl]methyl]butyric acid amide;
4-Oxo-4-(1-thien-2-yl-3,4-dihydroisoquinolin-2(1H)-yl)-N-(3-(trifluoromethyl)benzyl)butyric acid amide;
4-Oxo-4-[1-(4-pyridyl)-3,4-dihydro-1H-isoquinolin-2-yl]-N-[[3-(trifluoromethyl)phenyl]methyl]butyric acid amide;
4-(7-Fluoro-1-phenyl-3,4-dihydroisoquinolin-2(1H)-yl)-4-oxo-N-(3-(trifluoromethyl)benzyl)butyric acid amide;
4-(5-Fluoro-1-phenyl-3,4-dihydro-1H-isoquinolin-2-yl)-4-oxo-N-[[3-(trifluoromethyl)phenyl]methyl]butyric acid amide;
4-Oxo-4-(1-phenyl-3,4-dihydro-1H-isoquinolin-2-yl)-N-[[2-(trifluoromethyl)phenyl]methyl]butyric acid amide;
4-Oxo-4-(1-phenyl-3,4-dihydro-1H-isoquinolin-2-yl)-N-[[4-(trifluoromethyl)phenyl]methyl]butyric acid amide;
4-(4-Methyl-1-phenyl-3,4-dihydro-1H-isoquinolin-2-yl)-4-oxo-N-[[3-(trifluoromethyl)phenyl]methyl]butyric acid amide;
4-(4,4-Dimethyl-1-phenyl-1,3-dihydroisoquinolin-2-yl)-4-oxo-N-[[3-(trifluoromethyl)phenyl]methyl]butyric acid amide;
4-(7-Methoxy-1-phenyl-3,4-dihydro-1H-isoquinolin-2-yl)-4-oxo-N-[[3-(trifluoromethyl)phenyl]methyl]butyric acid amide;
4-(5-Methoxy-1-phenyl-3,4-dihydro-1H-isoquinolin-2-yl)-4-oxo-N-[[3-(trifluoromethyl)phenyl]methyl]butyric acid amide;
4-(3-Methyl-1-phenyl-3,4-dihydro-1H-isoquinolin-2-yl)-4-oxo-N-[[3-(trifluoromethyl)phenyl]methyl]butyric acid amide;
N-(2-Chlorophenyl)-4-oxo-4-(1-phenyl-3,4-dihydro-1H-isoquinolin-2-yl)butyric acid amide;
N-(2,1,3-Benzothiadiazol-4-yl)-4-oxo-4-(1-phenyl-3,4-dihydro-1H-isoquinolin-2-yl)butyric acid amide;
N-(1-Methyl-6-indazolyl)-4-oxo-4-(1-phenyl-3,4-dihydro-1H-isoquinolin-2-yl)butyric acid amide;
N-(2-Furylmethyl)-4-oxo-4-(1-phenyl-3,4-dihydro-1H-isoquinolin-2-yl)butyric acid amide;
N-Benzyl-4-oxo-4-(1-phenyl-3,4-dihydro-1H-isoquinolin-2-yl)butyric acid amide;
4-Oxo-4-(1-phenyl-3,4-dihydro-1H-isoquinolin-2-yl)-N-(2-pyridylmethyl)butyric acid amide;
N-[(4-Methoxyphenyl)methyl]-4-oxo-4-(1-phenyl-3,4-dihydro-1H-isoquinolin-2-yl)butyric acid amide;
4-Oxo-N-phenethyl-4-(1-phenyl-3,4-dihydro-1H-isoquinolin-2-yl)butyric acid amide;
4-Oxo-4-(1-phenyl-3,4-dihydro-1H-isoquinolin-2-yl)-N-(4-pyridylmethyl)butyric acid amide;
4-Oxo-4-(1-phenyl-3,4-dihydro-1H-isoquinolin-2-yl)-N-(3-phenylpropyl)butyric acid amide;
N-[2-(1H-Indol-3-yl)ethyl]-4-oxo-4-(1-phenyl-3,4-dihydro-1H-isoquinolin-2-yl)butyric acid amide;
4-(5,7-Dimethyl-1-phenyl-3,4-dihydro-1H-isoquinolin-2-yl)-N-(4-methoxyphenyl)-4-oxobutyric acid amide;
N-(2-Chlorophenyl)-4-(5,7-dimethyl-1-phenyl-3,4-dihydro-1H-isoquinolin-2-yl)-4-oxobutyric acid amide;
4-(5,7-Dimethyl-1-phenyl-3,4-dihydro-1H-isoquinolin-2-yl)-N-(1-methyl-6-indazolyl)-4-oxobutyric acid amide;

4-(5,7-Dimethyl-1-phenyl-3,4-dihydro-1H-isoquinolin-2-yl)-N-(2-furylmethyl)-4-oxobutyric acid amide;
N-Benzyl-4-(5,7-dimethyl-1-phenyl-3,4-dihydro-1H-isoquinolin-2-yl)-4-oxobutyric acid amide;
4-(5,7-Dimethyl-1-phenyl-3,4-dihydro-1H-isoquinolin-2-yl)-4-oxo-N-(2-pyridylmethyl)butyric acid amide;
4-(5,7-Dimethyl-1-phenyl-3,4-dihydro-1H-isoquinolin-2-yl)-N-[(4-methoxyphenyl)methyl]-4-oxobutyric acid amide;
4-(5,7-Dimethyl-1-phenyl-3,4-dihydro-1H-isoquinolin-2-yl)-4-oxo-N-phenethylbutyric acid amide;
4-(5,7-Dimethyl-1-phenyl-3,4-dihydro-1H-isoquinolin-2-yl)-4-oxo-N-(3-phenylpropyl)butyric acid amide;
N-(4-Methoxyphenyl)-4-(5-methyl-1-phenyl-3,4-dihydro-1H-isoquinolin-2-yl)-4-oxobutyric acid amide;
N-(2-Chlorophenyl)-4-(5-methyl-1-phenyl-3,4-dihydro-1H-isoquinolin-2-yl)-4-oxobutyric acid amide;
N-(1-Methyl-6-indazolyl)-4-(5-methyl-1-phenyl-3,4-dihydro-1H-isoquinolin-2-yl)-4-oxobutyric acid amide;
N-(2-Furylmethyl)-4-(5-methyl-1-phenyl-3,4-dihydro-1H-isoquinolin-2-yl)-4-oxobutyric acid amide;
N-Benzyl-4-(5-methyl-1-phenyl-3,4-dihydro-1H-isoquinolin-2-yl)-4-oxobutyric acid amide;
4-(5-Methyl-1-phenyl-3,4-dihydro-1H-isoquinolin-2-yl)-4-oxo-N-(2-pyridylmethyl)butyric acid amide;
N-[(4-Methoxyphenyl)methyl]-4-(5-methyl-1-phenyl-3,4-dihydro-1H-isoquinolin-2-yl)-4-oxobutyric acid amide;
4-(5-Methyl-1-phenyl-3,4-dihydro-1H-isoquinolin-2-yl)-4-oxo-N-phenethylbutyric acid amide;
4-(5-Methyl-1-phenyl-3,4-dihydro-1H-isoquinolin-2-yl)-4-oxo-N-(3-phenylpropyl)butyric acid amide;
N-(4-Methoxyphenyl)-4-(7-methyl-1-phenyl-3,4-dihydro-1H-isoquinolin-2-yl)-4-oxobutyric acid amide;
N-(2-Chlorophenyl)-4-(7-methyl-1-phenyl-3,4-dihydro-1H-isoquinolin-2-yl)-4-oxobutyric acid amide;
N-(1-Methyl-6-indazolyl)-4-(7-methyl-1-phenyl-3,4-dihydro-1H-isoquinolin-2-yl)-4-oxobutyric acid amide;
N-(2-Furylmethyl)-4-(7-methyl-1-phenyl-3,4-dihydro-1H-isoquinolin-2-yl)-4-oxobutyric acid amide;
N-Benzyl-4-(7-methyl-1-phenyl-3,4-dihydro-1H-isoquinolin-2-yl)-4-oxobutyric acid amide;
4-(7-Methyl-1-phenyl-3,4-dihydro-1H-isoquinolin-2-yl)-4-oxo-N-(2-pyridylmethyl)butyric acid amide;
N-[(4-Methoxyphenyl)methyl]-4-(7-methyl-1-phenyl-3,4-dihydro-1H-isoquinolin-2-yl)-4-oxobutyric acid amide;
4-(7-Methyl-1-phenyl-3,4-dihydro-1H-isoquinolin-2-yl)-4-oxo-N-phenethylbutyric acid amide;
4-(7-Methyl-1-phenyl-3,4-dihydro-1H-isoquinolin-2-yl)-4-oxo-N-(4-pyridylmethyl)butyric acid amide;
4-Oxo-4-(1-phenyl-3,4-dihydro-1H-isoquinolin-2-yl)-N-(2-thienylmethyl)butyric acid amide;
N-[(2-Chlorophenyl)methyl]-4-oxo-4-(1-phenyl-3,4-dihydro-1H-isoquinolin-2-yl)butyric acid amide;
N-[(2,4-Dichlorophenyl)methyl]-4-oxo-4-(1-phenyl-3,4-dihydro-1H-isoquinolin-2-yl)butyric acid amide;
N-[(3,4-Dichlorophenyl)methyl]-4-oxo-4-(1-phenyl-3,4-dihydro-1H-isoquinolin-2-yl)butyric acid amide;
4-Oxo-4-(1-phenyl-3,4-dihydro-1H-isoquinolin-2-yl)-N-(p-tolylmethyl)butyric acid amide;
N-(1,3-Benzodioxol-5-ylmethyl)-4-oxo-4-(1-phenyl-3,4-dihydro-1H-isoquinolin-2-yl)butyric acid amide;
N-[(3-Fluorophenyl)methyl]-4-oxo-4-(1-phenyl-3,4-dihydro-1H-isoquinolin-2-yl)butyric acid amide;
N-[(2-Fluorophenyl)methyl]-4-oxo-4-(1-phenyl-3,4-dihydro-1H-isoquinolin-2-yl)butyric acid amide;
N-[(4-Fluorophenyl)methyl]-4-oxo-4-(1-phenyl-3,4-dihydro-1H-isoquinolin-2-yl)butyric acid amide;
N-[(2,5-Difluorophenyl)methyl]-4-oxo-4-(1-phenyl-3,4-dihydro-1H-isoquinolin-2-yl)butyric acid amide;
N-(1-Naphthylmethyl)-4-oxo-4-(1-phenyl-3,4-dihydro-1H-isoquinolin-2-yl)butyric acid amide;
4-(7-Methyl-1-phenyl-3,4-dihydro-1H-isoquinolin-2-yl)-4-oxo-N-propylbutyric acid amide;
4-(5-Methyl-1-phenyl-3,4-dihydro-1H-isoquinolin-2-yl)-4-oxo-N-propylbutyric acid amide;
4-(5,7-Dimethyl-1-phenyl-3,4-dihydro-1H-isoquinolin-2-yl)-4-oxo-N-propylbutyric acid amide;
4-Oxo-4-(1-phenyl-3,4-dihydro-1H-isoquinolin-2-yl)-N-propylbutyric acid amide;
4-Oxo-4-(1-(2-tolyl)-3,4-dihydro-1H-isoquinolin-2-yl)-N-[[3-(trifluoromethyl)-phenyl]methyl]butyric acid amide;
4-Oxo-4-(1-(2-tolyl)-3,4-dihydro-1H-isoquinolin-2-yl)-N-[[4-(trifluoromethyl)-phenyl]methyl]butyric acid amide;
4-Oxo-4-(1-(2-tolyl)-3,4-dihydro-1H-isoquinolin-2-yl)-N-[[2-(trifluoromethyl)-phenyl]methyl]butyric acid amide;
4-Oxo-4-(1-(2-tolyl)-6-methyl-3,4-dihydro-1H-isoquinolin-2-yl)-N-[[3-(trifluoromethyl)-phenyl]methyl]butyric acid amide;
4-(1-(2-Methyl-prop-2-yl)-3,4-dihydro-1H-isoquinolin-2-yl)-4-oxo-N-[[3-(trifluoromethyl)phenyl]methyl]butyric acid amide;
4-(1-Cyclohexyl-3,4-dihydro-1H-isoquinolin-2-yl)-4-oxo-N-[[3-(trifluoromethyl)-phenyl]methyl]butyric acid amide; and
4-Oxo-4-(1-(2-fluorophenyl)-3,4-dihydro-1H-isoquinolin-2-yl)-N-[[3-(trifluoromethyl)phenyl]methyl]butyric acid amide;

or a physiologically compatible salt thereof.

11. A pharmaceutical composition comprising a therapeutically effective amount of at least one tetrahydroisoquinolinyl-4-oxobutyric acid amide compound as claimed in claim 1 and a pharmaceutically acceptable carrier, said compound being present in the form of an individual stereoisomer or a mixture thereof, a free compound and/or a physiologically compatible salt thereof, and said composition optionally further comprising suitable additives and/or auxiliary substances and/or optionally further active ingredients.

12. A method of treating a patient in need thereof for a condition, comprising administering to said patient an amount effective to treat said condition of at least one tetrahydroisoquinolinyl-4-oxobutyric acid amide compound as claimed in claim 1, said compound being in the form of an individual stereoisomer or a mixture thereof, the free compound and/or a physiologically compatible salt thereof, and said condition being selected from the group consisting of pain, epilepsy, urinary incontinence, anxiety states, dependency, mania, bipolar disorders, migraine, cognitive diseases, dystonia-associated dyskinesias and urinary incontinence.

13. A method of treating a patient in need thereof for a condition, comprising administering to said patient an amount effective to treat said condition of at least one tetrahydroisoquinolinyl-4-oxobutyric acid amide compound as claimed in claim 1, said compound being in the form of an individual stereoisomer or a mixture thereof, the free compound and/or a physiologically compatible salt thereof, said condition being selected from the group consisting of pain and epilepsy.

* * * * *